US010922362B2

(12) United States Patent
Blumenfeld et al.

(10) Patent No.: US 10,922,362 B2
(45) Date of Patent: Feb. 16, 2021

(54) MODELS FOR UTILIZING SILOED DATA

(71) Applicant: Clover Health, Jersey City, NJ (US)

(72) Inventors: Ian Blumenfeld, San Francisco, CA (US); Brian Johnson, San Francisco, CA (US); Brian Lucena, San Francisco, CA (US)

(73) Assignee: Clover Health, Jersey City, NJ (US)

( * ) Notice: Subject to any disclaimer, the term of this patent is extended or adjusted under 35 U.S.C. 154(b) by 269 days.

(21) Appl. No.: 16/029,405

(22) Filed: Jul. 6, 2018

(65) Prior Publication Data

US 2020/0012746 A1 Jan. 9, 2020

(51) Int. Cl.
| | | |
|---|---|---|
| *G06F 17/00* | (2019.01) | |
| *G06F 16/907* | (2019.01) | |
| *G06N 5/04* | (2006.01) | |
| *G16H 50/30* | (2018.01) | |
| *G06N 20/00* | (2019.01) | |

(52) U.S. Cl.
CPC ............. *G06F 16/907* (2019.01); *G06N 5/04* (2013.01); *G16H 50/30* (2018.01); *G06N 20/00* (2019.01)

(58) Field of Classification Search
None
See application file for complete search history.

(56) References Cited

U.S. PATENT DOCUMENTS

| | | | | |
|---|---|---|---|---|
| 2006/0112050 A1* | 5/2006 | Miikkulainen | ........ | G16H 50/20 706/46 |
| 2006/0129427 A1* | 6/2006 | Wennberg | .............. | G16H 50/30 705/2 |
| 2006/0173663 A1* | 8/2006 | Langheier | .............. | G16H 50/50 703/11 |
| 2008/0147441 A1* | 6/2008 | Kil | ........... | G06Q 50/24 705/2 |
| 2008/0177567 A1* | 7/2008 | Friedlander | ............ | G16H 50/30 705/2 |
| 2009/0326981 A1* | 12/2009 | Karkanias | .............. | G06Q 50/24 705/3 |
| 2012/0022644 A1* | 1/2012 | Reich | ................... | A61B 17/068 623/2.37 |
| 2012/0022844 A1* | 1/2012 | Teixeira | ............... | A61B 5/7214 703/11 |
| 2012/0109683 A1 | 5/2012 | Ebadollahi et al. | | |
| 2013/0211858 A1* | 8/2013 | Ohnemus | ............... | G16H 10/60 705/3 |
| 2013/0262357 A1* | 10/2013 | Amarasingham | ...... | G16H 50/70 706/21 |

(Continued)

OTHER PUBLICATIONS

The PCT Search Report and Written Opinion dated Sep. 19, 2019, for the PCT Application No. PCT/US19/39192, 8 pages.

*Primary Examiner* — Hansanul Mobin
(74) *Attorney, Agent, or Firm* — Lee & Hayes, P.C.

(57) ABSTRACT

Systems and methods for models utilizing siloed data are disclosed. For example, data stored with and/or available to one or more systems may be siloed such that it may not be aggregated and/or shared with other systems. The presently-disclosed systems and methods generate and utilize predictive layers and models to allow each system to predict outcomes using its own data and then models are shared between systems to allow each associated system to gain the benefits of the data of other systems without aggregating such data or otherwise sharing the data.

20 Claims, 11 Drawing Sheets

(56) References Cited

U.S. PATENT DOCUMENTS

| | | | |
|---|---|---|---|
| 2014/0095201 A1* | 4/2014 | Farooq | G16H 50/30 |
| | | | 705/3 |
| 2014/0280065 A1* | 9/2014 | Cronin | G06F 3/04842 |
| | | | 707/722 |
| 2016/0110505 A1* | 4/2016 | Symanski | H04L 67/32 |
| | | | 705/3 |
| 2016/0210555 A1* | 7/2016 | Murphy | G06N 5/022 |
| 2017/0357761 A1* | 12/2017 | Soto | G06Q 10/04 |
| 2018/0039731 A1* | 2/2018 | Szeto | G16B 20/00 |
| 2018/0060738 A1* | 3/2018 | Achin | G06Q 30/0201 |
| 2020/0012752 A1 | 1/2020 | Blumenfeld et al. | |

* cited by examiner

MODELS FOR UTILIZING SILOED DATA

BACKGROUND

Data from disparate sources may typically be aggregated and used. In some instances, data may be siloed and may not be aggregated with other data. Means to utilize siloed data without sharing the data may be desired. Described herein are improvements in technology and solutions to technical problems that can be used to, among other things, increase the availability and use of siloed data without sharing the data.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

DETAILED DESCRIPTION

Figure 1:
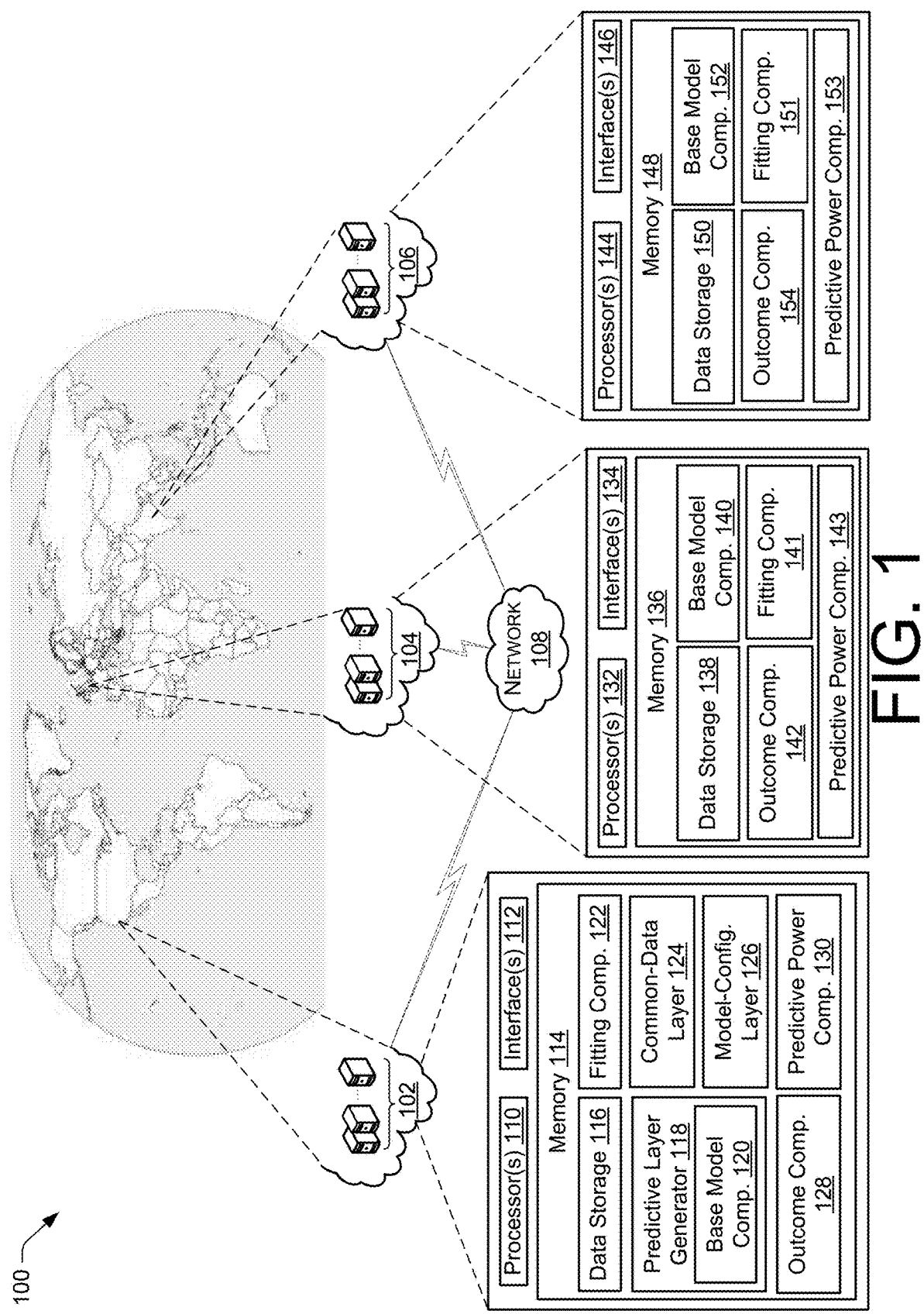
FIG. 1 illustrates a schematic diagram of an example environment for using models to share siloed data.

Systems and methods for models utilizing siloed data are described herein. Take, for example, multiple systems that store or otherwise access stored data. Each system may utilize its own data to, for example, predict desired or undesired outcomes. Also, if permitted and desired, the systems may agree to share data such that a given system may use its own data as well as data from other systems to predict outcomes. However, in some examples, data sharing between systems may be prohibited and/or not desired. For example, some governments enact laws and/or regulations that proscribe the sharing of data, such as the sharing of data across country boarders, across state/territory boarders, and/ or across company servers. In examples, firewalls may be setup and/or utilized that prevent the sharing of such data. Additionally, or alternatively, given the increased attention data sharing has garnered, companies and/or other entities may desire to silo their data even in the absence of government proscriptions. In these and other examples, the need arises to utilize siloed data without actually sending and/or receiving such data between systems.

The present innovation is directed to systems and methods that utilize generated models to use siloed data in a way that allows participating systems to gain the benefits of siloed data without that siloed data being transmitted in a proscribed and/or undesired way. By way of example, a first system and a second system may have siloed data but may desire to utilize each other's data to increase the ability and/or accuracy of predicting a given outcome. For example, the first and second systems may be entities that store and/or have access to health-related information of a number of members. The first and second system may be interested in predicting a certain health-related outcome, such as, for example, a likelihood that a member will be hospitalized.

In the example utilized above, the first system may have access to health-related data associated with its members and the second system may have access to different health-related data associated with its members. On their own, the first system and the second system could utilize their own data to predict a likelihood that a given member and/or set of members will be hospitalized. However, if both systems were able to utilize each other's data, the data sample size would increase and/or different categories of data (e.g., blood pressure, age, medical conditions, living conditions, etc.) would be available to the two systems, which may increase the accuracy of predicting the outcome. To utilize the siloed data from the first and second systems, one or more models may be generated and transmitted.

For example, the first system may have access to data of a first data type and data of a second data type. The first system may be configured to generate a first predictive layer that is fit to receive the data of the first and second data types and utilize that data to predict an outcome. The second system may have access to its own data, which may be of the first data type and of a third data type, for example. The first system may be configured to generate a second predictive layer that is fit to receive the second system's data types, and in this example, the first system may send the second predictive layer to the second system. The second system may then utilize the second predictive layer to predict the outcome. However, in this example, the first and second systems have a shared data type, namely the first data type. As such, both systems would benefit from utilizing the data each system has that is associated with the first data type.

To utilize such data, the first system may generate a third predictive layer that is fit to receive the second system's data associated with the first data type. The third predictive layer may be sent from the first system to the second system as a feature configured as an input to the second predictive layer. By so doing, the second system may now utilize its own data of the first data type and the third data type as well as the feature from the first system. Additionally, or alternatively, the second system may generate a fourth predictive layer that is fit to receive the first system's data associated with the first data type. The fourth predictive layer may be sent from the second system to the first system as another feature configured as an input to the first predictive layer. By so doing, the first system may now utilize its own data of the first data type and the second data type as well as the feature from the second system. The generation and use of predictive layers, as described herein, allows for each system to benefit from the siloed data of other associated systems without having to send and/or aggregate such siloed data.

By way of additional example, a third system may also desire to utilize the siloed data of the first and second systems, and the first and second systems may desire to utilize the siloed data of the third system. In these examples where three or more systems are involved, a predictive layer may be generated for each system. Each of the predictive layers may be fit to utilize data of the data types associated with the system for which the predictive layer was generated. Additionally, each system may be configured to generate a base model for one or more of the other associated systems. For example, the first system may be configured to generate a base model for the second system and another base model for the third system; the second system may be configured to generate a base model for the first system and another base model for the third system; and the third system may be configured to generate a base model for the first system and another base model for the second system. Each of these base models may be fit to utilize data types that are common between the sending system and the receiving system. A common-data layer may be generated and utilized to determine how the base models should be fit. The common-data layer may store information indicating which systems are associated with varying data types. Additionally, a model-configuration layer may store information indicating associations between system. The information from the common-data layer and the model-configuration layer may be utilized to determine which systems should generate base models and how those models should be fit.

The base models may be sent to their respective systems as features configured to be input into the predictive layer of a given system. In this way, each of the systems may utilize their own data and may also utilize the base models generated by the other associated systems as additional input to predict an outcome. As additional systems are associated with the existing systems, requests for base models may be transmitted to other associated systems and base models may be transmitted to and from the newly-associated system. By so doing, each associated system may utilize siloed data from the other systems without transferring such data and/or aggregating such data.

Additionally, or alternatively, one or more of the predictive layers and/or base models described herein may be fit based at least in part on historical data. For example, once an outcome is selected to be predicted, historical data indicating what data and/or data types may be relevant to predicting the outcome may utilized. The predictive layers and/or base models may be modified and/or otherwise configured, based at least in part on the historical data, to utilize the data and/or data types relevant to the outcome to predict the outcome.

Additionally, or alternatively, the systems described herein may be associated with different languages. For example, the first system may be associated with the English language while the second system may be associated with the Spanish language. A mapping may be performed between words and/or phrases of the first system and the second system such that both systems be communicate with each other and such that a determination of which data types are common to the two systems may be made.

Additionally, or alternatively, the systems and methods described herein may be configured to determine a relative importance of predictive layers and/or base models received from other systems. For example, the first system may receive a predictive layer and/or base model from another system that indicates a marginal, de minimus improvement in predictive power. In these examples, the system may determine that the information received from the other system is not worth keeping, such as for managing data storage needs. In other examples, the first system may determine that the information from the other system reduces the predictive power of the first system's predictive layer. In these examples, the first system may disregard the information from the other system, such as for performance upkeep. Additionally, or alternatively, in examples, information from another system may greatly improve the predictive power of a given predictive model. In these examples, such information may be weighted and/or otherwise favored by the predictive model and/or predictive models or other associated systems.

Additionally, or alternatively, the systems and methods described herein may be configured to determine that a given data type is more important and/or useful for predicting a given outcome than one or more other data types. For example, the addition of a given data type may increase the predictive power of the predictive layer and/or the removal of a given data type may decrease the predictive power of the predictive layer. In these examples, data may be generated that indicates the importance of the given data type. Communications may be sent to associated systems indicating the importance of the given data type, and for systems that are not associated with the data type (e.g., systems that do not collect such information or that have not been configured to analyze such information), they may be configured or reconfigured to collect and/or utilize the data type. By so doing, the predictive power of the predictive layers of those systems may be improved. Additionally, or alternatively, a given data type that is determined to be relatively unimportant may be noted and a communication may be sent to associated systems indicating that collection and/or use of data of that data type may cease and/or may not be used by the predictive layers of those systems. Additionally, or alternatively, a given system may generate results and/or models that are more useful than results and/or models generated by other systems. The relative importance of a given system to other associated systems may be determined and may be utilized to weight results and/or acquire additional participation by additional systems.

Additionally, or alternatively, the systems and methods described herein may be configured to switch outcomes to predict. Utilizing the example provided above, instead of predicting hospitalizations, one or more of the systems may desire to predict a different outcome, such as a likelihood of being diagnosed with diabetes. In these examples, the system desiring to predict the second outcome may have its predictive layer refit for input of data types relevant to predicting the diagnosis of diabetes. A request for base models may be sent to associated systems, and those systems may generate base models fit for the relevant data types. Those base models may be input as features to the newly-refit predictive layer and the second outcome may be predicted.

The present disclosure provides an overall understanding of the principles of the structure, function, manufacture, and use of the systems and methods disclosed herein. One or more examples of the present disclosure are illustrated in the accompanying drawings. Those of ordinary skill in the art will understand that the systems and methods specifically described herein and illustrated in the accompanying drawings are non-limiting embodiments. The features illustrated or described in connection with one embodiment may be combined with the features of other embodiments, including as between systems and methods. Such modifications and variations are intended to be included within the scope of the appended claims.

Additional details are described below with reference to several example embodiments.

FIG. 1 illustrates a schematic diagram of an example environment 100 for models utilizing siloed data. The environment 100 may include, for example, a first system 102, a second system, 104, and a third system 106. It should be understood that while FIG. 1 depicts three systems, the environment 100 may include two systems, three systems, or more than three systems. It should also be understood that while the objects are described as "systems," those objects may be considered devices. In examples, each of the systems 102, 104, 106 may be located in different locations. As shown in FIG. 1, for example, the first system 102 is located in the United States, the second system 104 is located in England, and the third system 106 is located in India. It should be understood that the systems described herein may be located in any location, and the locations depicted and described herein are by way of illustration only. Additionally, or alternatively, the systems may be located in the same location (e.g., the same address), but may be otherwise physically and/or digitally separated from each other, such as via firewalls. The systems 102, 104, 106 may be configured to communicate with each other via a network 108. The components of the systems 102, 104, 106 will be described in detail below.

For example, the first system 102 may include one or more processors 110, one or more network interfaces 112, and memory 114. The memory 114 may include one or more components, such as, for example, a data storage component 116, a predictive layer generator 118 (which may include a base model component 120), a fitting component 122, a common-data layer 124, a model-configuration layer 126, an outcome component 128, and/or a predictive power component 130. Each of the components of the memory 114 will be described below.

The data storage component 116 may be configured to store and/or access data associated with the first system 102. The data may be any data associated with the first system 102. In examples, the data may be siloed data. As used herein, "siloed data" includes data that is subject to laws, regulations, policies, and/or other restrictions and/or proscriptions that prevents, restricts, and/or proscribes sharing of that data with other systems, entities, and/or countries. Health-related data is used throughout this disclosure as an example of siloed data. However, it should be understood that the use of health-related data is by way of illustration only and not by way of limitation. In examples, the data stored by and/or accessible to a given system in the environment 100 may not be siloed. As such, some data may be siloed while other data may not be siloed. Alternatively, none of the data may be siloed but data aggregation may not be desired. The data storage component 116 may be utilized by one or more other components of the first system 102 to, for example, predict an outcome.

The predictive layer generator 118 may be configured to generate one or more predictive layers. A predictive layer may include one or more models that utilize predictive analytics to predict one or more outcomes. Predictive analytic techniques may include, for example, predictive modelling, machine learning, and/or data mining. Generally, predictive modelling may utilize statistics to predict outcomes. Machine learning, while also utilizing statistical techniques, may provide the ability to improve outcome prediction performance without being explicitly programmed to do so. A number of machine learning techniques may be employed to generate and/or modify the layers and/or models describes herein. Those techniques may include, for example, decision tree learning, association rule learning, artificial neural networks (including, in examples, deep learning), inductive logic programming, support vector machines, clustering, Bayesian networks, reinforcement learning, representation learning, similarity and metric learning, sparse dictionary learning, and/or rules-based machine learning.

Information from stored and/or accessible data may be extracted from one or more databases, such as for example the data storage 116, and may be utilized to predict trends and behavior patterns. In examples, the event, otherwise described herein as an outcome, may be an event that will occur in the future, such as whether a member will be hospitalized, a likelihood of a member being diagnosed with diabetes, a likelihood of a member missing a medication prescription fill at a pharmacy, etc. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis, such as from the data storage 116.

Data analysis may include using one or more models, including for example one or more algorithms, to inspect the data with the goal of identifying useful information and arriving at one or more determinations that assist in predicting the outcome of interest. One or more validation operations may be performed, such as using statistical analysis techniques, to validate accuracy of the models. Thereafter predictive modelling may be performed to generate accurate predictive models for future events. By so doing, the predictive layer generator 118 may utilize data from the data storage 116, as well as features from other systems as described herein, to predict or otherwise determine an outcome. Outcome prediction may be deterministic such that the outcome is determined to occur or not occur. Additionally, or alternatively, the outcome prediction may be probabilistic such that the outcome is determined to occur to a certain probability and/or confidence.

The first system 102 may generate predictive layers, via the predictive layer generator 118, based at least in part on at least one of the data to be utilized by the predictive layer, the data type of the data to be utilized by the predictive layer, the outcome selected to be predicted, and/or one or more specifications of the system indicated to utilize the predictive layer. Once generated, the predictive layer may be packaged and/or formatted such that it may be transmitted and/or utilized by another system, such as the second system 104 and/or the third system 106. For example, the predictive layer may be packaged as a Docker image and may be transmitted to the second system 104 and/or the third system 106 in response to a pull request from the second system 104 and/or the third system 106. Additionally, or alternatively, the predictive layer may be pushed to the second system 104 and/or the third system 106 from the first system 104. The packaging may include operating-system-level virtualization, also described as containerization. Resource isolation features of the Linux kernel such as cgroups and kernel namespaces, and a union-capable file system, may be utilized to allow independent containers to run within a Linux instance, which may allow for operations without the use of virtual machines. In other examples, virtual machines may be generated and/or utilized. One or more application programming interfaces (APIs) may be included and may be utilized by a system to predict outcomes with the predictive layer.

The fitting component 122 may be configured to fit one or more predictive layers. Predictive layer fitting may be based at least in part on historical data. For example, once an outcome is selected to be predicted, historical data indicating what data and/or data types may be relevant to predicting the outcome may be utilized. The predictive layers and/or base models may be modified and/or otherwise configured, based at least in part on the historical data, to utilize the data and/or data types relevant to the outcome to predict the outcome. Model fitting by the fitting component 122 may include techniques such as linear regression and/or nonlinear regression. Once fit, the predictive layer may be sent to other systems and utilized by those systems.

The outcome component 128 may be configured to utilize the generated predictive layer to predict the selected outcome. For example, data available to the system running the predictive layer may be retrieved and input into the predictive layer. The outcome component 128 may run the one or more models associated with the predictive layer to determine the selected outcome. In examples, the outcome may be deterministic or probabilistic, as described herein.

The base model component 120 of the predictive layer generator 118 may be configured to generate base models for other systems. As used herein, "base models" may be the same as or similar to predictive layers and/or may include the same or similar functionality. Base models, as described herein, may be generated and/or utilized when three or more systems are associated, as will be described in more detail below with respect to FIG. 3. Base models may be generated in response to a request for a base model from another system. Using FIG. 1 as an example, the second system 104 and the third system 106 may request a base model from the first system 102. The request, and/or other information available to the first system 102, may indicate the data and/or data types to be utilized by the second system 104 and by the third system 106.

A base model for the second system 104 may be generated and fit based at least in part on overlapping data types between the first system 102 and the second system 104. For example, a common-data layer 124 may store information indicating which data types are available to the systems. Using the common-data layer 124, a determination may be made as to the data types available to the second system 104 that are also available to the first system 102. A base model configured to utilize data of the overlapping data types may be generated by the base model component 120 and may be fit by the fitting component 122. In examples, the base model may be utilized to predict the outcome using the data of the first system 102.

The result of that analysis may include a determination of the outcome and/or one or more serialized models and/or log files. Serialized models may include translated data structures and/or object states in a format that can be stored and/or transmitted for reconstruction by the receiving system. The serialized object may include a coefficient mapping for common data types between systems as well as a resource configured to allow the receiving system to utilize the coefficient mapping with respect to its data of the common data types. Log files include indications of events that occur in an operating system, such as the resulting prediction from the first system 102 running the base model. In examples, the base model may be formatted as a feature configured as an input to a predictive model of the system utilizing the base model. The feature may be an individual measurable property or characteristic of the observed outcome. The feature may be numeric and/or may include one or more strings and/or graphs. In examples, the feature may correspond to an explanatory variable, such as when statistical techniques are utilized when generating and/or utilizing predictive models. The features may be utilized as inputs by the predictive models of each system to predict the outcome, as described herein.

Base models may be generated by some or all of the systems of the environment 100. For example, the first system 102 may include its base model component 120, the second system 104 may include its base model component 140, and/or the third system 106 may include its base model component 152. The base model component 140 of the second system 104 and/or the base model component 152 of the third system 106 may include the same or similar components as the base model component 120 of the first system 102 and/or may perform the same or similar operations.

A model-configuration layer 126 may be configured to store information indicating associations between systems. For example, the model-configuration layer 126 may be configured to indicate that the first system 102 is associated with the second system 104, the first system 102 is associated with the third system 106, the second system 104 is associated with the first system 102, the second system 104 is associated with the third system 106, the third system 106 is associated with the first system 102, and/or the third system 106 is associated with the second system 104. The model-configuration layer 126 may be utilized to determine which systems may generate base models for other systems when a request for such base models is received. The model-configuration layer 126 may be additionally configured to determine a mapping between words and/or phrases in different languages. For example, the systems of the environment 100 may be configured to run based on different languages, such as English, Spanish, etc. A mapping between words and phrases may be generated and utilized to determine, for example, the overlap between data types available to each system and/or the outcome selected for prediction. In examples, the model-configuration layer 126 may be a separate component from the common-data layer 124. In other examples, the model-configuration layer 126 and the common-data layer 124 may be parts of the same component, which may be described as a management layer.

The predictive power component 130 may be configured to determine a change in the predicted outcome, such as, for example, an increase or decrease in a probability of the outcome occurring, based on utilizing a feature from a base model. For example, some features may have a large impact on determining the outcome based at least in part on the amount of data available to the system running the base model, the accuracy of the base model, etc. The first system 102 may be configured to utilize the predictive power component 130 to determine an amount of change of the probability of the outcome occurring based at least in part on utilizing the feature as an input. In examples, when the amount of change is greater than a threshold amount, such as, for example, a 1% increase, the feature may be utilized as an input for the predictive model. In other examples where the amount of change is less than the threshold amount, the feature may be disregarded. In still other examples, the feature may result in a negative change to the outcome probability, and in these examples, the feature may be disregarded.

The predictive power component 130 may be additionally, or alternatively, configured to determine one or more data types that impact the outcome probability and an amount of such impact. For example, the predictive power component 130 may determine that a first data type impacts the outcome probability greatly while a second data type has little impact on the outcome probability. In these examples, the predictive power component 130 may determine that the first data type impacts the outcome probability by at least a threshold amount, for example by 1%. A directive may then be generated and/or sent to systems that do not currently acquire data of the first type. The directive may request that the system initiate acquisition of such data to increase the accuracy of outcome determination. In other examples, a determination may be made that an instance of the outcome without using a particular data type results in a determined confidence within a threshold confidence range of another instance of the outcome that does use the particular data type. In these examples, the particular data type may be determined to be not of importance to determining the outcome, and the data associated with the data type may be removed from the system and/or may not be utilized by the system to predict the outcome. By so doing, computing resources are saved in that data that is less meaningful to determining the outcome is not utilized and/or is discarded.

The predictive power component 130 may be additionally, or alternatively, configured to determine a confidence at which an outcome is determined based at least in part on a feature from a given system. In examples where the confidence exceeds a threshold confidence, it may be determined that the results of a given system are useful enough to utilize for other associated systems. This determination may be system-to-system specific. For example, the feature from the second system 104 as utilized by the first system 102 may not be as useful to the first system 102 while the feature from the second system 104 to the third system 106 may increase the confidence of the determined outcome above the threshold confidence level and may thus be useful to the third system 106.

The second system 104 may include components that may be the same as or similar to the components of the first system 102. For example, the second system 104 may include one or more processors 132, one or more interfaces 134, and memory 136. Each of these components may function in the same or a similar manner from the one or more processors 110, the one or more interfaces 112, and/or memory 114 of the first system 102. The memory 136 of the second system 104 may include components such as, for example, a data storage component 138, a predictive layer generator 139, a base model component 140, an outcome component 142, a fitting component 141, and/or a predictive power component 143. These components may function in the same or a similar manner to the data storage 116, predictive layer generator 118, base model component 120, outcome component 128, fitting component 122, and/or predictive power component 130 of the first system 102. For example, the data storage 138 may store or otherwise access data associated with and/or available to the second system 104. The predictive layer generator 139 may generate predictive layers associated with the second system 104. The base model component 140 may generate base models requested from other systems. The outcome component 142 may utilize one or more predictive layers and features from other systems to determine a selected outcome.

The third system 106 may include components that may be the same as or similar to the components of the first system 102. For example, the third system 106 may include one or more processors 144, one or more interfaces 146, and memory 148. Each of these components may function in the same or a similar manner from the one or more processors 110, the one or more interfaces 112, and/or memory 114 of the first system 102. The memory 148 of the third system 106 may include components such as, for example, a data storage component 150, a predictive layer generator 151, a base model component 152, an outcome component 154, a fitting component 151, and/or a predictive power component 153. These components may function in the same or a similar manner to the data storage 116, predictive layer generator 118, base model component 120, outcome component 128, fitting component 122, and predictive power component 130 of the first system 102. For example, the data storage 150 may store or otherwise access data associated with and/or available to the third system 106. The predictive layer generator 151 may generate predictive layers associated with the third system 106. The base model component 152 may generate base models requested from other systems. The outcome component 154 may utilize one or more predictive layers and features from other systems to determine a selected outcome.

While certain components are illustrated and described above as specific to a given system, such as the first system 102, it should be understood that some or all of the components may be associated with one or more of the other systems, such as the second system 104 and/or the third system 106. Additionally, operations performed by the processors 110 of the first system 102 may also, or alternatively, be performed by one or more of the processors 132 of the second system 104 and/or one or more of the processors 144 of the third system 106.

As used herein, a processor, such as processor(s) 110, 132, and/or 144, may include multiple processors and/or a processor having multiple cores. Further, the processors may comprise one or more cores of different types. For example, the processors may include application processor units, graphic processing units, and so forth. In one implementation, the processor may comprise a microcontroller and/or a microprocessor. The processor(s) 110, 132, and/or 144 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 110, 132, and/or 144 may possess its own local memory, which also may store program components, program data, and/or one or more operating systems.

The memory 114, 136, and/or 148 may include volatile and nonvolatile memory, removable and non-removable media implemented in any method or technology for storage of information, such as computer-readable instructions, data structures, program component, or other data. Such memory 114, 136, and/or 148 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 114, 136, and/or 148 may be implemented as computer-readable storage media ("CRSM"), which may be any available physical media accessible by the processor(s) 104 and/or 130 to execute instructions stored on the memory 114, 136, and/or 148. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Further, functional components may be stored in the respective memories, or the same functionality may alternatively be implemented in hardware, firmware, application specific integrated circuits, field programmable gate arrays, or as a system on a chip (SoC). In addition, while not illustrated, each respective memory, such as memory 114, 136, and/or 148, discussed herein may include at least one operating system (OS) component that is configured to manage hardware resource devices such as the network interface(s), the I/O devices of the respective apparatuses, and so forth, and provide various services to applications or components executing on the processors. Such OS component may implement a variant of the FreeBSD operating system as promulgated by the FreeBSD Project; other UNIX or UNIX-like variants; a variation of the Linux operating system as promulgated by Linus Torvalds; the FireOS operating system from Amazon.com Inc. of Seattle, Wash., USA; the Windows operating system from Microsoft Corporation of Redmond, Wash., USA; LynxOS as promulgated by Lynx Software Technologies, Inc. of San Jose, Calif.; Operating System Embedded (Enea OSE) as promulgated by ENEA AB of Sweden; and so forth.

The network interface(s) 112, 134, and/or 146 may enable communications between the components and/or devices shown in environment 100 and/or with one or more other remote systems, as well as other networked devices. Such network interface(s) 112, 134, and/or 146 may include one or more network interface controllers (NICs) or other types of transceiver devices to send and receive communications over the network 108.

For instance, each of the network interface(s) 112, 134, and/or 146 may include a personal area network (PAN) component to enable communications over one or more short-range wireless communication channels. For instance, the PAN component may enable communications compliant with at least one of the following standards IEEE 802.15.4 (ZigBee), IEEE 802.15.1 (Bluetooth), IEEE 802.11 (WiFi), or any other PAN communication protocol. Furthermore, each of the network interface(s) 112, 134, and/or 146 may include a wide area network (WAN) component to enable communication over a wide area network.

Figure 2:
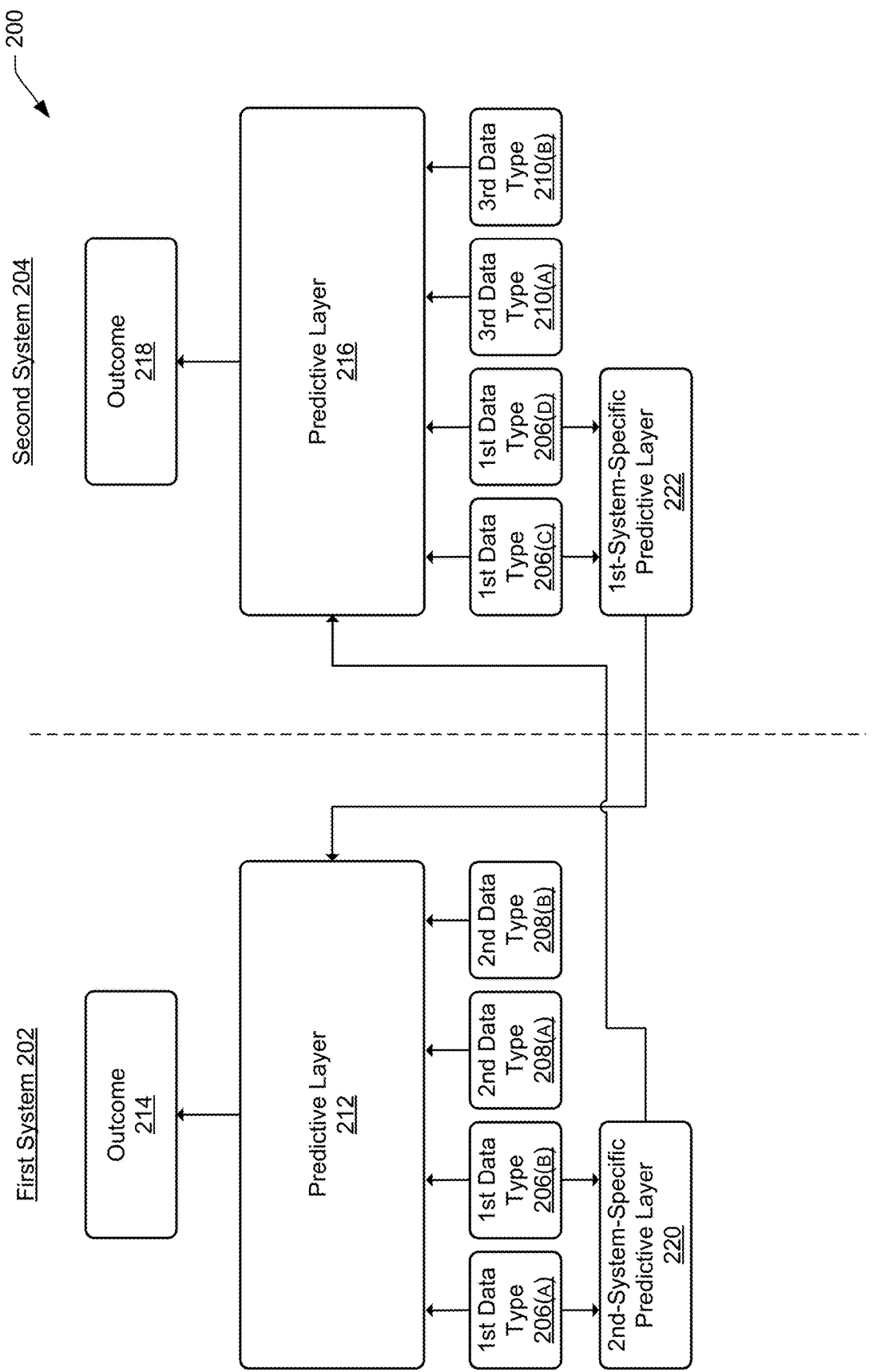
FIG. 2 illustrates a conceptual diagram of example components of two systems storing siloed and/or sharable data.

FIG. 2 illustrates a conceptual diagram of example components and data of two systems storing siloed and/or sharable data. The environment 200 depicted in FIG. 2 shows a first system 202 and a second system 204. The first system 202 may include the same or similar components and perform the same or similar operations as the first system 102 from FIG. 1. The second system 204 may include the same or similar components and perform the same or similar operations as the second system 104 and/or the third system 106 from FIG. 1.

With respect to the first system 202, it may include and/or have access to data of various data types. As shown in FIG. 2, the data may include data of a first data type 206(a)-(b) and data of a second data type 208(a)-(b). With respect to the second system 204, it may include and/or have access to data of the first data type 206(c)-(d) and data of a third data type 210(a)-(b). In the example described with respect to FIG. 2, the data accessible to the first system 202 may be different from the data accessible to the second system 204. For example, the first system 202 may have data related to a first set of patients (otherwise referred to as members) while the second system 204 may have data related to a second set of members. That data may be of data types such as, for example, blood pressure, age, weight, body-mass index, diagnosed conditions, etc. Thus, while both system have data related to different members, both systems may have data of the same type, shown in FIG. 2 as the first data type 206(a)-(d). Additionally, both systems may have data of different types, shown in FIG. 2 as the second data type 208(a)-(b) for the first system 202 and the third data type 210(a)-(b) for the second system 204.

The first system 202 may also include a predictive layer 212 that may be fit to receive the data of the first data type 206(a)-(b) and the data of the second data type 208(a)-(b) and utilize that data to predict Outcome A 214. The first system 202 may be configured to generate a second predictive layer 216 that is fit to receive the second system's 204 data types 206(c)-(d) and 210(a)-(b), and the first system 202 may send the second predictive layer 216 to the second system 204. The second system 204 may then utilize the second predictive layer 216 to predict Outcome B 218. In this example, the first system 202 utilizes its own data to generate Outcome A 214, and the second system 204 utilizes its own data to generate Outcome B 218, but the first system 202 does not utilize the data from the second system 204, or vice versa. However, both systems would benefit from utilizing the data each system has that is associated with a common data type, here illustrated as the first data type 206(a)-(d). It should be understood that Outcome A and Outcome B may be the same outcome or different outcomes.

To utilize such data, the first system 202 may generate a third predictive layer, illustrated as the second-system-specific predictive layer 220, that is fit to receive the second system's 204 data associated with the first data type 206(c)-(d). The third predictive layer 220 may be sent from the first system 202 to the second system 204 as a feature configured as an input to the second predictive layer 216, as described above with respect to FIG. 1, for example. By so doing, the second system 204 may now utilize its own data of the first data type 206(c)-(d) and the third data type 210(a)-(b) as well as the feature from the first system 202.

Additionally, or alternatively, the second system 204 may generate a fourth predictive layer 222, illustrated as the first-system-specific predictive layer 222, that is fit to receive the first system's 202 data associated with the first data type 206(a)-(b) and data associated with the second data type 208(a)-(b). The fourth predictive layer 222 may be sent from the second system 204 to the first system 202 as another feature configured as an input to the first predictive layer 212. By so doing, the first system 202 may now utilize its own data of the first data type 206(a)-(b) and the second data type 208(a)-(b) as well as the feature from the second system 204. The generation and use of predictive layers, as described herein, allows for each system to benefit from the siloed data of other associated systems without having to send and/or aggregate such siloed data.

Use of features between the first system 202 and the second system 204 may include ensembling at least one of the features with the predictive layers of the systems. The ensembling may include combining two or more algorithms associated with the predictive layers to allow for incorporation of predictions from each of the algorithms. The ensembling may include, for example, techniques such as averaging, majority-vote methods, weighted-average methods, bootstrap aggregation, boosting, and/or stacking.

Figure 3:
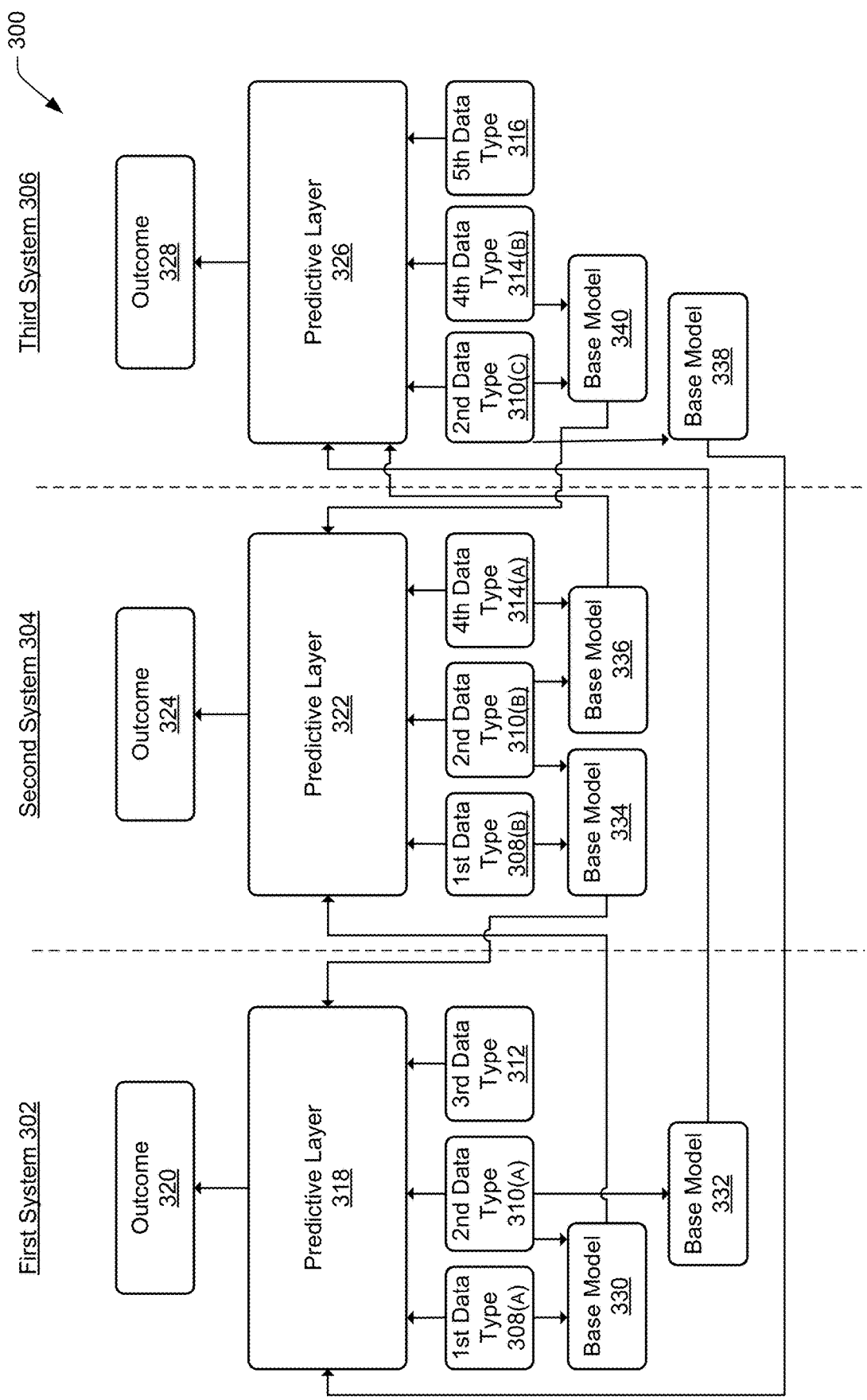
FIG. 3 illustrates a conceptual diagram of example components of multiple systems storing siloed and/or sharable data.

FIG. 3 illustrates a conceptual diagram of example components and data of multiple systems storing siloed and/or sharable data. The environment 300 depicted in FIG. 3 shows a first system 302, a second system 304, and a third system 306. The first system 302 may include the same or similar components and perform the same or similar operations as the first system 102 from FIG. 1. The second system 304 may include the same or similar components and perform the same or similar operations as the second system 104 from FIG. 1. The third system 306 may include the same or similar components and perform the same or similar operations as the third system 106 from FIG. 1.

With respect to the first system 302, it may include and/or have access to data of various data types. As shown in FIG. 3, the data may include data of a first data type 308(*a*), data of a second data type 310(*a*), and data of a third type 312. With respect to the second system 304, it may include and/or have access to data of the first data type 308(*b*), data of the second data type 310(*b*), and data of a fourth data type 314(*a*). With respect to the third system 306, it may include and/or have access to data of the second data type 310(*c*), data of the fourth data type 314(*b*), and data of a fifth data type 316. In the example described with respect to FIG. 3, the data accessible to the first system 302 may be different from the data accessible to the second system 304 and/or the third system 306. For example, the first system 302 may have data related to a first set of members, the second system 304 may have data related to a second set of members, and the third system 306 may have data related to a third set of members. That data may be of data types such as, for example, blood pressure, age, weight, body-mass index, diagnosed conditions, etc. Thus, while all three systems have data related to different members, each system may have data of the same type, shown in FIG. 3 as the second data type 310(*a*)-(*c*). Additionally, the systems may have data of different types, shown in FIG. 3 as the third data type 312 for the first system 302 and the fifth data type of the third system 306. Additionally, some systems may have overlapping data while others may not. For example, the first data type 308(*a*)-(*b*) overlaps with respect to the first system 302 and the second system 304, but not with respect to the third system 306.

The first system 302 may also include a predictive layer 318 that may be fit to receive the data of the first data type 38(*a*), the data of the second data type 310(*a*), and the data of the third data type 312, and utilize that data to predict Outcome A 320. The first system 302 may be configured to generate a second predictive layer 322 that is fit to receive the second system's 204 data types 308(*b*), 310(*b*), and 314(*a*), and the first system 302 may send the second predictive layer 322 to the second system 304. The second system 304 may then utilize the second predictive layer 322 to predict Outcome B 324. The first system 302 may be configured to generate a third predictive layer 326 that is fit to receive the third system's 306 data types 310(*c*), 314(*b*), and 316, and the first system 302 may send the third predictive layer 326 to the third system 306. The third system 306 may then utilize the third predictive layer 326 to predict Outcome C 328. It should be understood that Outcome A 320, Outcome B 324, and Outcome C 328 may be the same outcome or the outcomes may differ.

In this example, the first system 302 utilizes its own data to generate Outcome A 320, the second system 304 utilizes its own data to generate Outcome B 324, and the third system 306 utilizes its own data to generate Outcome C 328, but the first system 302 does not utilize the data from the second system 304 or the third system 306, the second system 304 does not utilize the data from the first system 302 or the third system 306, and the third system 306 does not utilize the data from the first system 302 or the second system 304. However, the systems would benefit from utilizing the data each system has that is associated with a common data type. For example, the first data type 308(*a*)-(*b*) is common as between the first system 302 and the second system 304, the second data type 310(*a*)-(*c*) is common as between all three systems 302, 304, 306, and the fourth data type 314(*a*)-(*b*) is common as between the second system 304 and the third system 306.

To utilize data of common data types between systems, the systems may be configured to generate one or more base models for sharing between the systems. A base model component of each system may be configured to generate base models for other systems. Base models may be generated in response to a request for a base model from another system. Using FIG. 3 as an example, the second system 304 and the third system 306 may request a base model from the first system 302. The request, and/or other information available to the first system 302, may indicate the data and/or data types to be utilized by the second system 304 and by the third system 306.

A base model 330 for the second system 304 may be generated and fit based at least in part on overlapping data types between the first system 302 and the second system 304. For example, a common-data layer may store information indicating which data types are available to the systems. Using the common-data layer, a determination may be made as to the data types available to the second system 304 that are also available to the first system 302, here illustrated as the first data type 308(*a*)-(*b*) and the second data type 310(*a*)-(*b*). A base model configured to utilize data of the overlapping data types may be generated by the base model component and may be fit. In examples, the base model may be utilized to predict O Outcome A 320 using the data of the first system 302 of the common data types.

The result of that analysis may include a determination of the outcome and/or one or more serialized models and/or log files. Serialized models may include translated data structures and/or object states in a format that can be stored and/or transmitted for reconstruction by the receiving system. The serialized object may include a coefficient mapping for common data types between systems as well as a resource configured to allow the receiving system to utilize the coefficient mapping with respect to its data of the common data types. Log files include indications of events that occur in an operating system, such as the resulting prediction from the first system 302 running the base model 330. In examples, the base model 330 may be formatted as a feature configured as an input to the predictive model 322 of the second system 304. The feature may be an individual measurable property or characteristic of the observed outcome. The feature may be numeric and/or may include one or more strings and/or graphs. In examples, the feature may correspond to an explanatory variable, such as when statistical techniques are utilized when generating and/or utilizing predictive models. The features may be utilized as inputs by the predictive models of each system to predict the outcome, as described herein.

Base models may be generated by some or all of the systems of the environment 300. For example, the first system 302 may generate the base model 330 for the second system 304, the first system 302 may generate a base model 332 for the third system 306, the second system 304 may generate a base model 334 for the first system 302, the second system 304 may generate a base model 336 for the third system 306, the third system 306 may generate a base model 338 for the first system 302, and/or the third system 306 may generate a base model 340 for the second system 304.

A model-configuration layer may be configured to store information indicating associations between systems. For example, the model-configuration layer may be configured to indicate that the first system 302 is associated with the second system 304, the first system 302 is associated with the third system 306, the second system 304 is associated with the first system 302, the second system 304 is associated with the third system 306, the third system 306 is associated with the first system 302, and/or the third system 306 is associated with the second system 304. The model-configuration layer may be utilized to determine which systems may generate base models for other systems when a request for such base models is received. The model-configuration layer may be additionally configured to determine a mapping between words and/or phrases in different languages. For example, the systems of the environment 300 may be configured to run based on different languages, such as English, Spanish, etc. A mapping between words and phrases may be generated and utilized to determine, for example, the overlap between data types available to each system and/or the outcome selected for prediction. In examples, the model-configuration layer may be a separate component from the common-data layer. In other examples, the model-configuration layer and the common-data layer may be parts of the same component, which may be described as a management layer.

Figure 4:
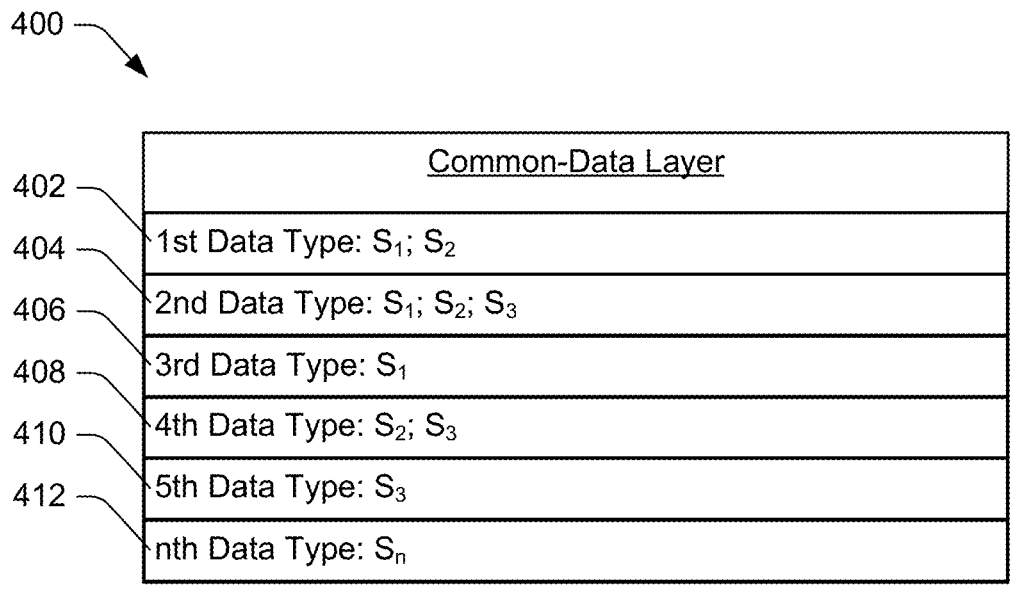
FIG. 4 illustrates a common-data layer for models utilizing siloed data.

FIG. 4 illustrates a common-data layer 400 for models utilizing siloed data. The common-data layer 400 may be the same as or similar to the common-data layer 124 from FIG. 1. The common-data layer 400 may also perform the same or similar functions as the common-data layer 124 from FIG. 1. For example, the common-data layer 400 may include one or more databases that store and/or otherwise access information indicating data types associated with one or more associated systems. As described herein, multiple systems may be associated with each other and may be configured to communicate with each other. However, at least a portion of these systems may have siloed data that may not be shared with other systems. The systems and methods described herein may utilize predictive models to utilize such siloed data without sharing and/or aggregating data across systems.

In examples where three or more systems are associated, the common-data layer 400 may be generated. The common-data layer 400 may receive indications of the data types associated with the various associated systems, and may store associations between those data types and the various systems. By way of example, and as illustrated in FIG. 4, the common-data layer 400 may include a number of data-type entries 402-412 that list the data types and the systems associated therewith. For example, the first data-type entry 402 indicates that the first data type is associated with a first system and a second system; the second data-type entry 404 indicates that the second data type is associated with the first system, the second system, and the third system; the third data-type entry 406 indicates that the third data type is associated with the first system; the fourth data-type entry 408 indicates that the fourth data type is associated with the second system and the third system; the fifth data-type entry 410 indicates that the fifth data type is associated with the third system; and the nth data-type entry 412 indicates that the nth data type is associated with the nth system.

The common-data layer 400 may be accessed by one or more components of the system to determine, for example, how to generate base models for the various systems. As described above, base models may be generated that are fit based on common data types associated with the sending and receiving systems. Using FIG. 4 as an example, a request from the second system for base models will result in a base model being generated by the first system that is fit to predict an outcome based on data of the first data type and the second data type in light of the information provided by the common-data layer 400. A base model may also be generated by the third system that is fit to predict the outcome based on data of the second type and the fourth type in light of the information provided by the common-data layer 400.

The common-data layer 400 may be updated continuously and/or periodically and/or in response to an event occurring, such as adding a system and/or removing a system and/or a system indicating the addition or removal of a data type. Additionally, or alternatively, when a determination is made that a given system and/or data type does not positively effect prediction of outcomes, such as above a threshold level, the common-data layer 400 may be updated to remove the entry associated with that data type. It should be understood that data types may have various nomenclature and/or may be expressed in multiple languages and/or abbreviations. For example, "blood pressure" may be expressed by some systems as "BP," "B.P.," and/or "presión sanguinea." The common-data layer 400 and/or one or more other components of the system may be configured to associate nomenclatures, languages, and abbreviations.

Figure 5:
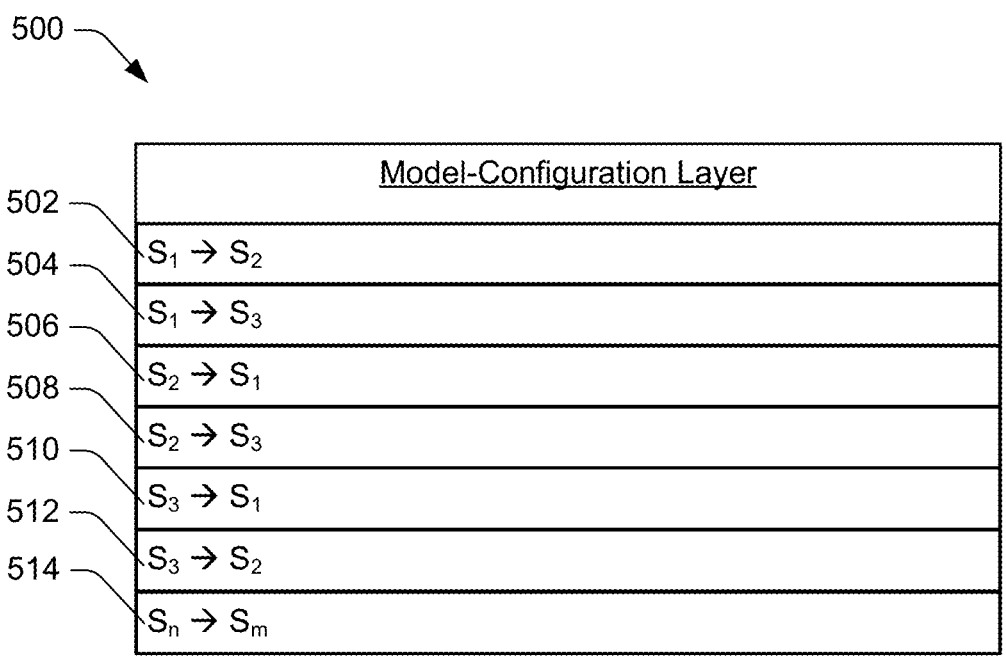
FIG. 5 illustrates a model-configuration layer for models utilizing siloed data.

FIG. 5 illustrates a model-configuration layer 500 for models utilizing siloed data. The model-configuration layer 500 may be the same as or similar to the model-configuration layer 126 from FIG. 1. The model-configuration layer 500 may also perform the same or similar functions as the model configuration layer 126 from FIG. 1. For example, the model-configuration layer 500 may include one or more databases that store and/or otherwise access information indicating which systems are associated with each other. As described herein, multiple systems may be associated with each other and may be configured to communicate with each other. However, at least a portion of these systems may have siloed data that may not be shared with other systems. The systems and methods described herein may utilize predictive models to utilize such siloed data without sharing and/or aggregating data across systems.

In examples where three or more systems are associated, the model-configuration layer 500 may be generated. The model-configuration layer may have one or more system-association entries 502-514 that may indicate which systems are configured to send and/or receive base models for predicting an outcome. Using FIG. 5 as an example, the first system-association entry 502 may indicate that a first system is configured to send base models to a second system; the second system-association entry 504 may indicate that the first system is configured to send base models to a third system; the third system-association entry 506 may indicate that the second system is configured to send base models to the first system; the fourth system-association entry 508 may indicate that the second system is configured to send base models to the third system; the fifth system-association entry 510 may indicate that the third system is configured to send base models to the first system; the sixth system-association entry 512 may indicate that the third system is configured to send base models to the second system; and the seventh system-association entry 514 may indicate that the nth system is configured to send base models to the mth system.

The model-configuration layer 500 may be accessed by one or more components of the system to determine, for example, which systems may generate base models and to which systems those models may be sent. The model-configuration layer 500 may be updated continuously and/or periodically and/or in response to an event occurring, such as adding a system and/or removing system and/or a system indicating restrictions on sending and/or receiving base models from other systems. Additionally, or alternatively, when a determination is made that a given system does not positively effect prediction of outcomes, such as above a threshold level, the model-configuration layer 500 may be updated to remove the entry associated with that system.

FIGS. 6-12 illustrate various processes for models utilizing siloed data. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-5, although the processes may be implemented in a wide variety of other environments, architectures and systems.

Figure 6:
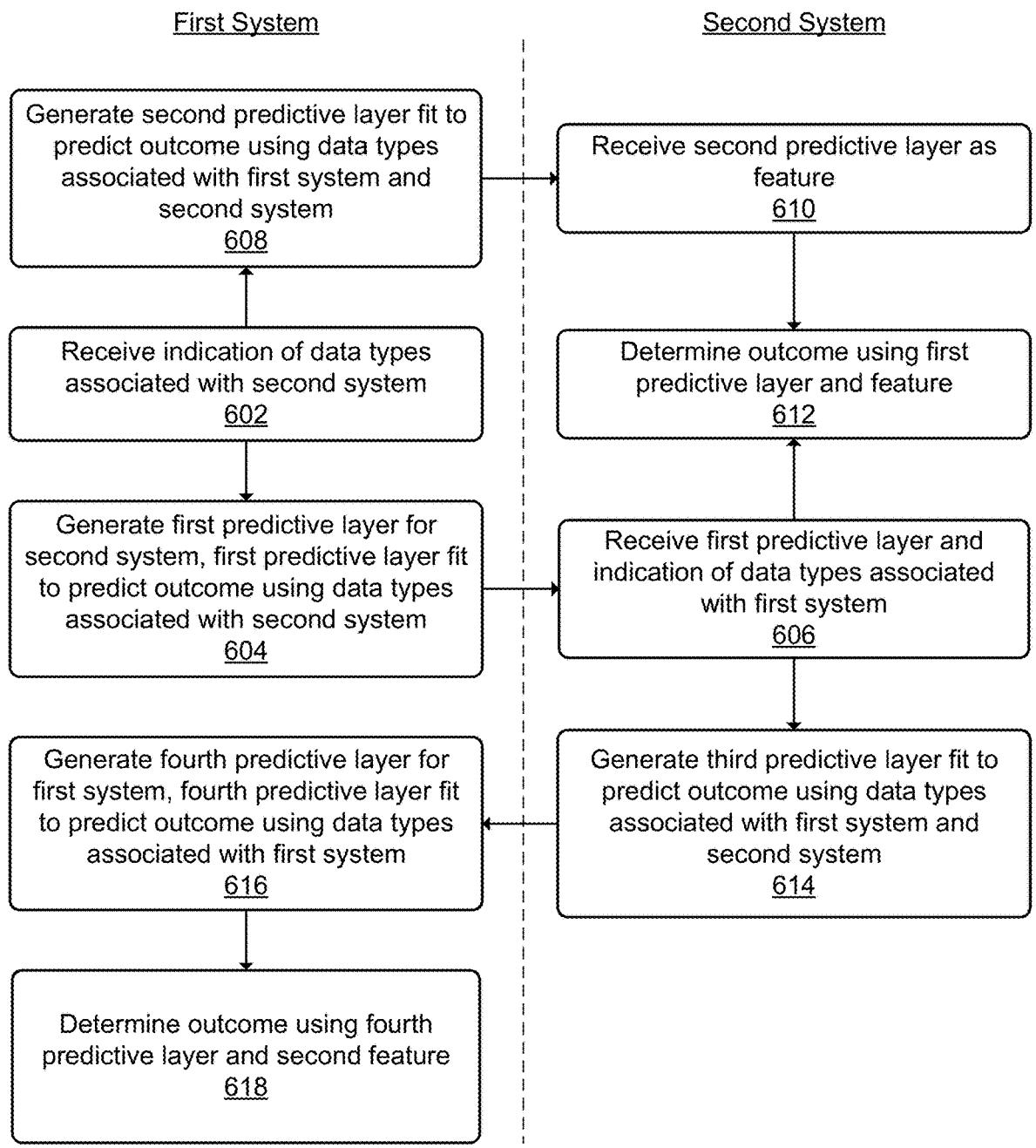
FIG. 6 illustrates a flow diagram of an example process for models utilizing siloed data between two systems.

FIG. 6 illustrates a flow diagram of an example process 600 for modeled data sharing between two systems storing siloed data. The order in which the operations or steps are described is not intended to be construed as a limitation, and any number of the described operations may be combined in any order and/or in parallel to implement process 600. As shown in FIG. 6, the operations described with respect to the process 600 may be performed by a first system and a second system, for example. Example operations performed by each system are shown in FIG. 6.

At block 602, the process 600 may include the first system receiving an indication of data types associated with the second system. For example, data associated with the first system and separate data associated with the second system may be of various data types. For example, the first system may have data related to a first set of patients (otherwise referred to as members) while the second system may have data related to a second set of members. That data may be of data types such as, for example, blood pressure, age, weight, body-mass index, diagnosed conditions, etc. Thus, while both systems have data related to different members, both systems may have data of the same type. Additionally, both systems may have data of different types. The first system may be configured to determine the data types available to the second system and/or the second system or another system may send an indication of the data types to the first system.

At block 604, the process 600 may include the first system generating and sending a predictive-layer configuration based on the indication of data types available to the second system. The predictive-layer configuration may include a file that may include pseudo code that specifies how to transform data into inputs for the modeling system as well as information indicating what data and data types may be used as well as what types of models may be fit.

At block 606, the process 600 may include the second system generating a first predictive layer fit to predict an outcome using data types associated with the second system. The first predictive layer may be generated by a predictive layer generator of the first system and may be fit to predict an outcome using data types associated with the second system. A predictive layer may include one or more models that utilize predictive analytics to predict one or more outcomes. Predictive analytic techniques may include, for example, predictive modelling, machine learning, and/or data mining, as described more fully herein.

Information from stored and/or accessible data may be extracted from one or more databases and may be utilized to predict trends and behavior patterns. In examples, the event, otherwise described herein as an outcome, may be an event that will occur in the future, such as whether a member will be hospitalized, a likelihood of a member being diagnosed with diabetes, a likelihood of a member missing a medication prescription fill at a pharmacy, etc. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis.

The second system may generate the first predictive layer based at least in part on at least one of the data to be utilized by the predictive layer, the data type of the data to be utilized by the predictive layer, the outcome selected to be predicted, and/or one or more specifications of the system indicated to utilize the predictive layer. Once generated, the predictive layer may be packaged and/or formatted such that it may be transmitted and/or utilized by another system, such as the second system.

At block 608, the process 600 may include the first system generating a second predictive layer fit to predict the outcome using data types associated with the first system and the second system. Generation of the second predictive layer may be performed in the same or a similar manner as described with respect to block 606, except that the second predictive layer may be configured or otherwise fit to utilize data of data types that are associated with both the first system and the second system, otherwise described herein as common data types.

At block 610, the process 600 may include the second system receiving the second predictive layer as a feature from the first system. The feature may be an individual measurable property or characteristic of the observed outcome. The feature may be numeric and/or may include one or more strings and/or graphs. In examples, the feature may correspond to an explanatory variable, such as when statistical techniques are utilized when generating and/or utilizing predictive models. The features may be utilized as inputs by the predictive models of each system to predict the outcome, as described herein.

At block 612, the process 600 may include the second system determining the outcome using the first predictive layer and the feature. Data analysis may include using one or more models, including for example one or more algorithms, to inspect the data with the goal of identifying useful information and arriving at one or more determinations that assist in predicting the outcome of interest. One or more validation operations may be performed, such as using statistical analysis techniques, to validate accuracy of the models. Thereafter predictive modelling may be performed to generate accurate predictive models for future events. By so doing, the second system may utilize data available to it, as well as features from other systems as described herein, to predict or otherwise determine an outcome. Outcome prediction may be deterministic such that the outcome is determined to occur or not occur. Additionally, or alternatively, the outcome prediction may be probabilistic such that the outcome is determined to occur to a certain probability and/or confidence.

At block 614, the process 600 may include the second system generating a third predictive layer fit to predict the outcome using data types associated with the first system and the second system. Generating the third predictive layer may be performed in the same or a similar manner as described above with respect to block 608 above.

At block 616, the process 600 may include the first system generating a fourth predictive layer for the first system. The fourth predictive layer may be fit to predict the outcome using data types associated with the first system. Generating the fourth predictive layer may be performed in the same or a similar manner as generation of the first predictive layer as described with respect to block 604, above.

At block 618, the process 600 may include the first system determining the outcome using the fourth predictive layer and a second feature corresponding to the third predictive layer. The data analysis may be the same as or similar to that described with respect to block 612, above. By so doing, the first system may utilize a predictive layer configured and fit for its data and its data types while also utilizing, as a feature, the third predictive layer from the second system. Likewise, the second system may utilize a predictive layer configured and fit for its data and its data types while also utilizing, as another feature, the second predictive layer from the first system.

Figure 7:
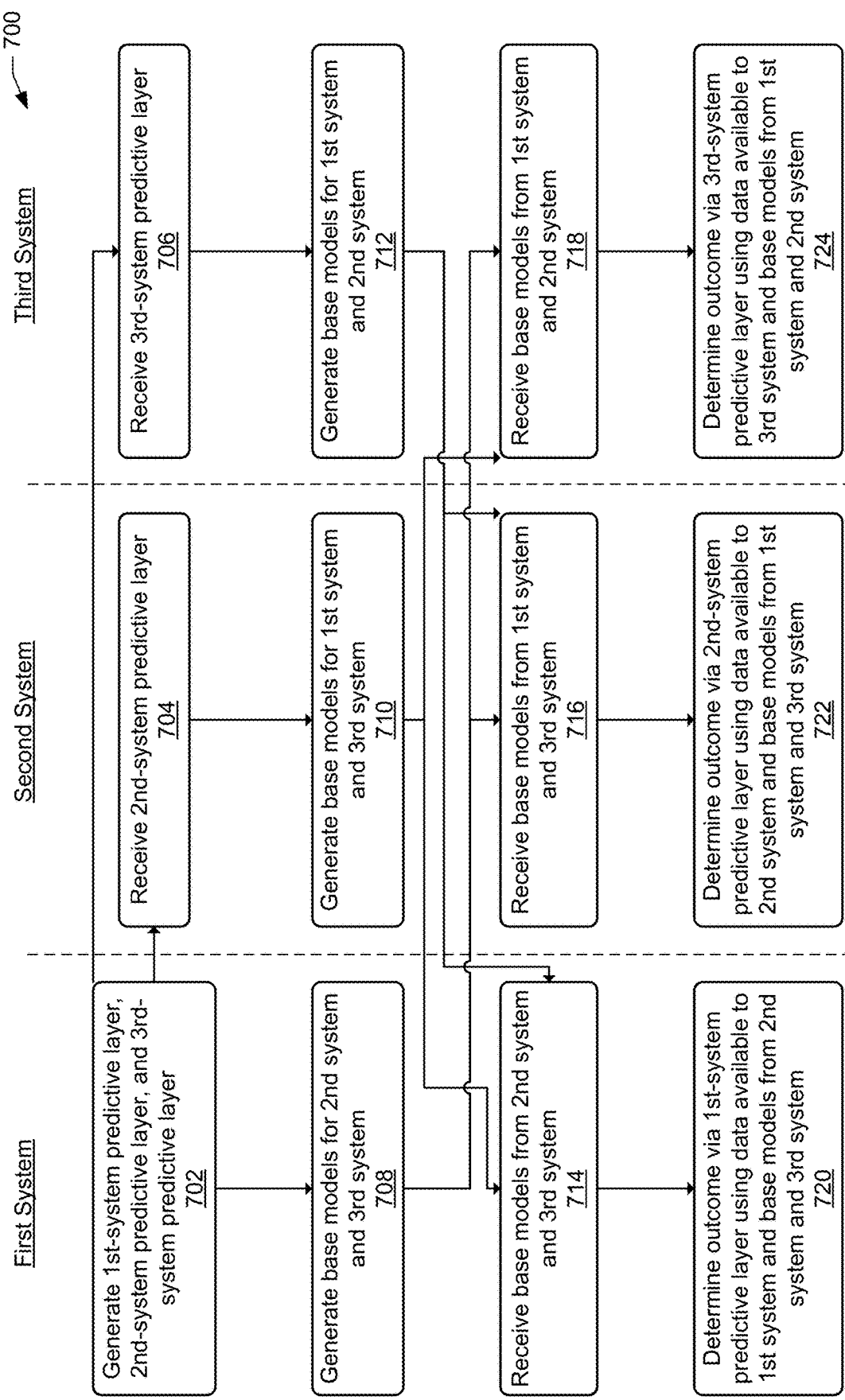
FIG. 7 illustrates a flow diagram of an example process for models utilizing siloed data between three or more systems.

FIG. 7 illustrates a flow diagram of an example process 700 for modeled data sharing between three or more systems storing siloed and/or sharable data. The order in which the operations or steps are described is not intended to be construed as a limitation, and any number of the described operations may be combined in any order and/or in parallel to implement process 700. As shown in FIG. 7, the operations described with respect to the process 700 may be performed by a first system, a second system, and/or a third system, for example. Example operations performed by each system are shown in FIG. 7.

At block 702, the process 700 may include the first system generating a first-system predictive layer. The predictive layers may be generated by a predictive layer generator of the first system and may be fit to predict an outcome using data types associated with the system the predictive layer is intended for. A predictive layer may include one or more models that utilize predictive analytics to predict one or more outcomes. Predictive analytic techniques may include, for example, predictive modelling, machine learning, and/or data mining, as described more fully herein.

Information from stored and/or accessible data may be extracted from one or more databases and may be utilized to predict trends and behavior patterns. In examples, the event, otherwise described herein as an outcome, may be an event that will occur in the future, such as whether a member will be hospitalized, a likelihood of a member being diagnosed with diabetes, a likelihood of a member missing a medication prescription fill at a pharmacy, etc. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis.

The first system may generate the predictive layer based at least in part on at least one of the data to be utilized by the predictive layer, the data type of the data to be utilized by the predictive layer, the outcome selected to be predicted, and/or one or more specifications of the system indicated to utilize the predictive layer. Once generated, the predictive layer may be packaged and/or formatted such that it may be transmitted and/or utilized by another system, such as the second system and/or the third system.

At block 704, the process 700 may include the second system generating a second-system predictive layer. Generation of the second-system predictive layer may be performed in the same or a similar manner as generation of the first-system predictive layer. In examples, a predictive-layer configuration, as described more fully herein, may be sent from the first system to the second system to allow for and/or aid in generation of the second-system predictive layer.

At block 706, the process 700 may include the third system generating a third-system predictive layer. Generation of the third-system predictive layer may be performed in the same or a similar manner as generation of the first-system predictive layer. In examples, a predictive-layer configuration, as described more fully herein, may be sent from the first system to the third system to allow for and/or aid in generation of the third-system predictive layer.

At block 708, the process 700 may include the first system generating base models for the second system and the third system. As used herein, "base models" may be the same as or similar to predictive layers and/or may include the same or similar functionality. Base models, as described herein, may be generated and/or utilized when three or more systems are associated, as described herein. Base models may be generated in response to a request for a base model from another system. Using FIG. 7 as an example, the second system and the third system may request a base model from the first system. The request, and/or other information available to the first system, may indicate the data and/or data types to be utilized by the second system and by the third system.

A base model for the second system may be generated and fit based at least in part on overlapping data types between the first system and the second system. For example, a common-data layer may store information indicating which data types are available to the systems. Using the common-data layer, a determination may be made as to the data types available to the second system that are also available to the first system. A base model configured to utilize data of the overlapping data types may be generated by the base model component and may be fit by a fitting component. In examples, the base model may be utilized to predict the outcome using the data of the first system. Additionally, a base model for the third system may be generated and fit based at least in part on overlapping data types between the first system and the third system.

At block 710, the process 700 may include the second system generating base models for the first system and the third system. For example, a base model for the first system may be generated and fit based at least in part on overlapping data types between the first system and the second system. Likewise, a base model for the third system may be generated and fit based at least in part on overlapping data types between the second system and the third system.

At block 712, the process 700 may include the third system generating base models for the first system and the second system. For example, a base model for the first system may be generated and fit based at least in part on overlapping data types between the first system and the third system. Likewise, a base model for the second system may be generated and fit based at least in part on overlapping data types between the second system and the third system.

At block 714, the process 700 may include the first system receiving base models from the second system and from the third system. The base models may be received as features. A feature may be an individual measurable property or characteristic of the observed outcome. The feature may be numeric and/or may include one or more strings and/or graphs. In examples, the feature may correspond to an explanatory variable, such as when statistical techniques are utilized when generating and/or utilizing predictive models. The features may be utilized as inputs by the predictive models of each system to predict the outcome, as described herein.

At block 716, the process 700 may include the second system receiving base models from the first system and the third system. The base models may be received as features as described with respect to block 714, above.

At block 718, the process 700 may include the third system receiving base models from the first system and the second system. The base models may be received as features as described with respect to block 714, above.

At block 720, the process 700 may include the first system determining an outcome via the first-system predictive layer using data available to the first system and base models from the second system and the third system. Data analysis may include using one or more models, including for example one or more algorithms, to inspect the data with the goal of identifying useful information and arriving at one or more determinations that assist in predicting the outcome of interest. One or more validation operations may be performed, such as using statistical analysis techniques, to validate accuracy of the models. Thereafter predictive modelling may be performed to generate accurate predictive models for future events. By so doing, the first system may utilize data available to it, as well as features from other systems as described herein, to predict or otherwise determine an outcome. Outcome prediction may be deterministic such that the outcome is determined to occur or not occur. Additionally, or alternatively, the outcome prediction may be probabilistic such that the outcome is determined to occur to a certain probability and/or confidence At block 722, the process 700 may include the second system determining the outcome via the second-system predictive layer using data available to the second system and base models from the first system and the third system.

At block 724, the process 700 may include the third system determining the outcome via the third-system predictive layer using data available to the third system and base models from the first system and the second system.

Figure 8:
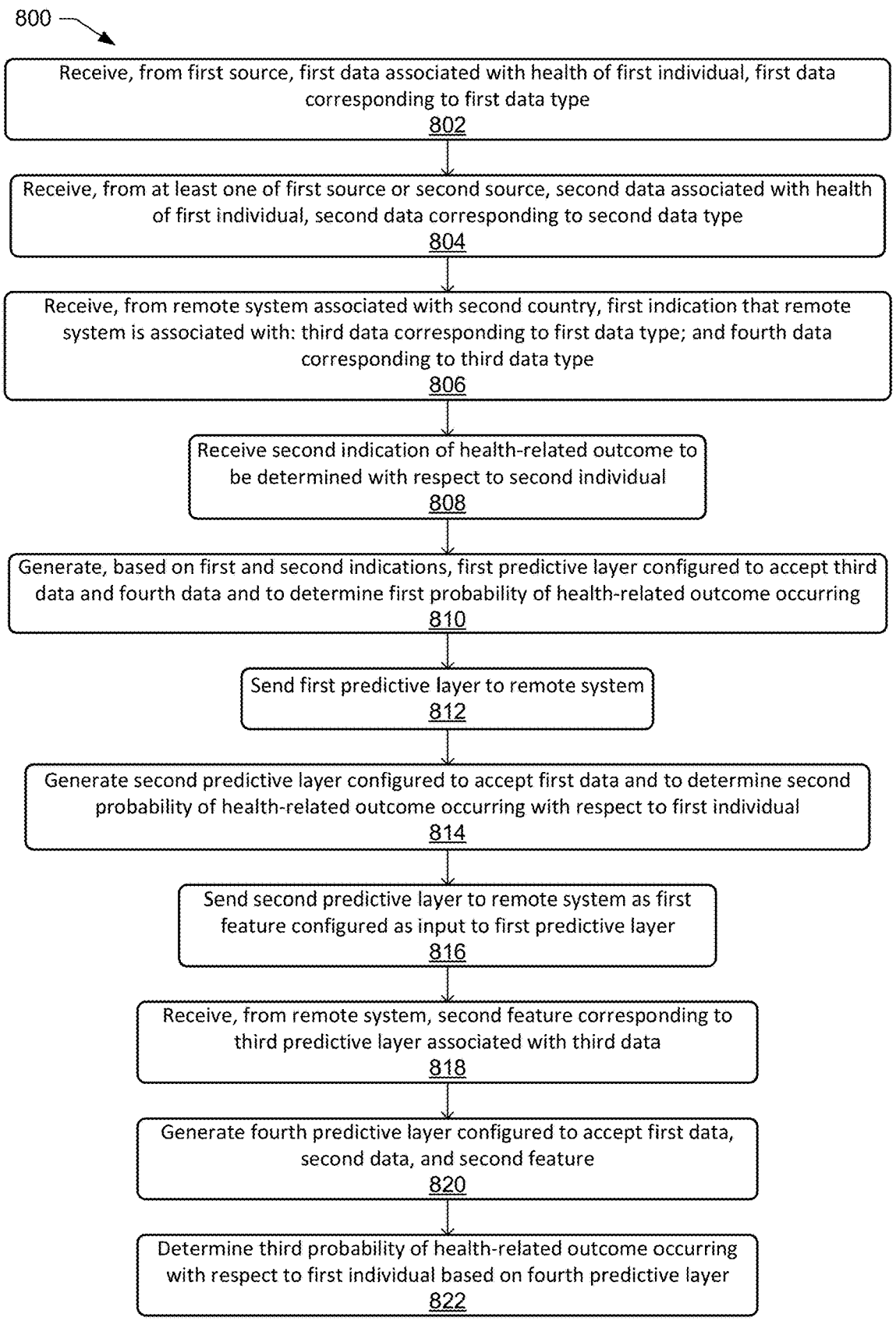
FIG. 8 illustrates a flow diagram of an example process for models utilizing siloed data.

FIG. 8 illustrates a flow diagram of an example process 800 for models utilizing siloed data. The order in which the operations or steps are described is not intended to be construed as a limitation, and any number of the described operations may be combined in any order and/or in parallel to implement process 800.

At block 802, the process 800 may include receiving, from a first source associated with a first country, first data associated with health of a first individual, the first data corresponding to a first data type. The first source may be a system and/or database associated with entities that acquire health-related data, such as, for example, hospitals, clinics, practitioners, patients, health insurance companies, etc. The first country may be any country in which the first source is located. It should be understood that the first source may be located in an area not designated as a country, and in these situations, the first source may be associated with a first environment. The data may be of data types such as, for example, blood pressure, age, weight, body-mass index, diagnosed conditions, etc.

At block 804, the process 800 may include receiving, from at least one of the first source or a second source associated with the first country, second data associated with the health of the first individual, the second data corresponding to a second data type.

At block 806, the process 800 may include receiving, from a remote system associated with a second country, a first indication that the remote system is associated with at least one of (1) third data associated with health of a second individual, the third data corresponding to the first data type, or (2) fourth data associated with the health of the second individual, the fourth data corresponding to a third data type. For example, the first system may store and/or access data associated with patients and/or members associated with the first system while the remote system (otherwise described as a second system) may store and/or access data associated with patients and/or members associated with the remote system. Both systems may have access to data sharing a common data type and both systems may have access to data with disparate data types. In these examples, the data from at least one of the systems may be siloed such that the data may not be transferred outside of the country in which the data resides and/or outside of the servers on which the data resides.

At block 808, the process 800 may include receiving a second indication of a health-related outcome to be determined with respect to the second individual. For example, the remote system may indicate that a health-related outcome is to be determined. Such a health-related outcome may include, for example, a likelihood that an individual will be hospitalized, be diagnosed with a certain condition, etc.

At block 810, the process 800 may include sending, to the remote system, a predictive-layer configuration including pseudo code configured for use by the remote system to generate a first predictive layer configured to accept the third data and the fourth data and to determine a first probability of the health-related outcome occurring with respect to the second individual. A predictive layer may include one or more models that utilize predictive analytics to predict one or more outcomes. Predictive analytic techniques may include, for example, predictive modelling, machine learning, and/or data mining, as described above.

Information from stored and/or accessible data may be extracted from one or more databases and may be utilized to predict trends and behavior patterns. In examples, the event, otherwise described herein as an outcome, may be an event that will occur in the future, such as whether a member will be hospitalized, a likelihood of a member being diagnosed with diabetes, a likelihood of a member missing a medication prescription fill at a pharmacy, etc. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis Data analysis may include using one or more models, including for example one or more algorithms, to inspect the data with the goal of identifying useful information and arriving at one or more determinations that assist in predicting the outcome of interest. One or more validation operations may be performed, such as using statistical analysis techniques, to validate accuracy of the models. Thereafter, predictive modelling may be performed to generate accurate predictive models for future events.

At block 812, the process 800 may include generating, based on the remote system being associated with the third data and receiving the first data, a second predictive layer configured to accept the first data and to determine a second probability, based on the first data, of the health-related outcome occurring with respect to the first individual. Generation of the second predictive layer may be performed in the same or a similar manner as the first predictive layer, as described above.

At block 814, the process 800 may include sending the second predictive layer to the remote system. The second predictive layer may be configured to generate a first feature configured as an input to the first predictive layer. Sending the second predictive layer may be performed in the same or a similar manner as sending the first predictive layer as described above.

At block 816, the process 800 may include receiving, from the remote system, a third predictive layer configured to generate a second feature. The feature may be an individual measurable property or characteristic of the observed outcome. The feature may be numeric and/or may include one or more strings and/or graphs. In examples, the feature may correspond to an explanatory variable, such as when statistical techniques are utilized when generating and/or utilizing predictive models. The features may be utilized as inputs by the predictive models of each system to predict the outcome, as described herein.

At block 818, the process 800 may include generating a fourth predictive layer configured to accept the first data, the second data, and the second feature. Generation of the fourth predictive layer may be performed in the same or a similar manner as described above with respect to other predictive layers.

At block 820, the process 800 may include determining a third probability of the health-related outcome occurring with respect to the first individual based on the fourth predictive layer. By so doing, the outcome may be predicted using not only the data available to the first system, but also the feature provided by the second system without aggregating the siloed data from the second system.

The process 800 may additionally, or alternatively, include generating a serialized object corresponding to the second predictive layer. The serialized object may include a coefficient mapping for the first data type and a resource configured to allow the remote system to utilize the coefficient mapping with respect to the third data. In these examples, sending the second predictive layer as the first feature comprises sending the serialized object to the remote system. When features correspond to serialized objects, as described herein, ensembling of the serialized object with a predictive layer may be performed as described herein.

The process 800 may additionally, or alternatively, include fitting one or more of the predictive layers based at least in part on data available to the system utilizing a particular predictive layer and/or the features utilized by the particular predictive layer and/or historical data associated with data types utilized by the particular predictive layer.

Figure 9:
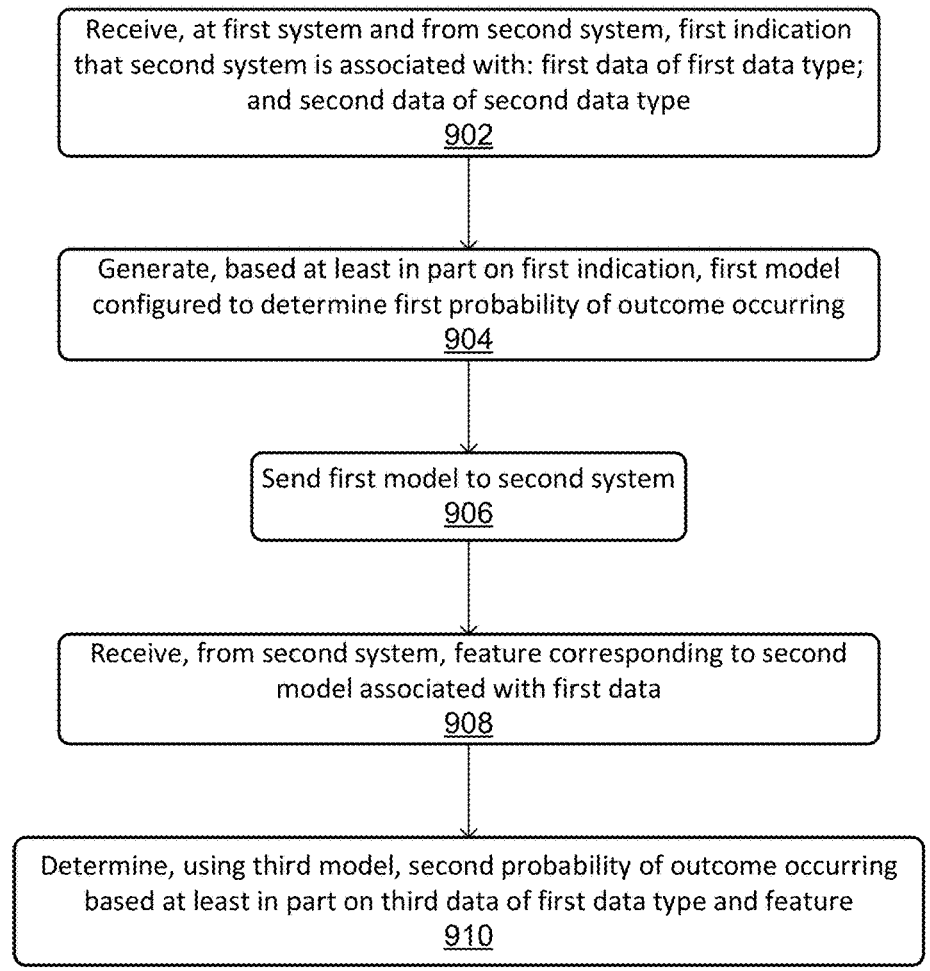
FIG. 9 illustrates a flow diagram of another example process for models utilizing siloed data.

FIG. 9 illustrates a flow diagram of another example process 900 for models utilizing siloed data. The order in which the operations or steps are described is not intended to be construed as a limitation, and any number of the described operations may be combined in any order and/or in parallel to implement process 900.

At block 902, the process 900 may include receiving, at a first system and from a second system, an indication that the second system is associated with (1) first data of a first data type, and (2) second data of a second data type. For example, the first system may store and/or access data associated with patients and/or members associated with the first system while the second system may store and/or access data associated with patients and/or members associated with the second system. Both systems may have access to data sharing a common data type and both systems may have access to data with disparate data types. In these examples, the data from at least one of the systems may be siloed such that the data may not be transferred outside of the country in which the data resides and/or outside of the servers on which the data resides.

At block 904, the process 900 may include generating, based at least in part on the indication, a first model configured to determine whether outcome occurs. The model may utilize predictive analytics to predict one or more outcomes. Predictive analytic techniques may include, for example, predictive modelling, machine learning, and/or data mining, as described above.

Information from stored and/or accessible data may be extracted from one or more databases and may be utilized to predict trends and behavior patterns. In examples, the event, otherwise described herein as an outcome, may be an event that will occur in the future, such as whether a member will be hospitalized, a likelihood of a member being diagnosed with diabetes, a likelihood of a member missing a medication prescription fill at a pharmacy, etc. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis Data analysis may include using one or more models, including for example one or more algorithms, to inspect the data with the goal of identifying useful information and arriving at one or more determinations that assist in predicting the outcome of interest. One or more validation operations may be performed, such as using statistical analysis techniques, to validate accuracy of the models. Thereafter, predictive modelling may be performed to generate accurate predictive models for future events.

At block 906, the process 900 may include sending the first model to the second system. For example, the model may be packaged as a Docker image and may be transmitted to the second system in response to a pull request from the second system. Additionally, or alternatively, the model may be pushed to the second system from the first system. The packaging may include operating-system-level virtualization, also described as containerization. Resource isolation features of the Linux kernel such as cgroups and kernel namespaces, and a union-capable file system, may be utilized to allow independent containers to run within a Linux instance, which may allow for operations without the use of virtual machines. In other examples, virtual machines may be generated and/or utilized. One or more APIs may be included and may be utilized by a system to predict outcomes with the model.

At block 908, the process 900 may include receiving, from the second system, a second model configured to generate associated with the first data. The feature may be an individual measurable property or characteristic of the observed outcome. The feature may be numeric and/or may include one or more strings and/or graphs. In examples, the feature may correspond to an explanatory variable, such as when statistical techniques are utilized when generating and/or utilizing predictive models. The features may be utilized as inputs by the predictive models of each system to predict the outcome, as described herein.

At block 910, the process 900 may include determining, using a third model, whether an outcome occurs based at least in part on third data of the first data type and the feature. By so doing, the outcome may be predicted using not only the data available to the first system, but also the feature provided by the second system without aggregating the siloed data from the second system.

The process 900 may additionally, or alternatively, include generating a serialized object corresponding to the second model. The serialized object may include a coefficient mapping for the first data type and a resource configured to allow the second system to utilize the coefficient mapping with respect to the data. In these examples, sending the second model as the feature comprises sending the serialized object to the second system. When features correspond to serialized objects are sent, as described herein, ensembling of the serialized object with a model may be performed as described herein.

The process 900 may additionally, or alternatively, include fitting one or more of the models based at least in part on data available to the system utilizing a particular model and/or the features utilized by the particular model and/or historical data associated with data types utilized by the particular model.

The process 900 may additionally, or alternatively, include determining a mapping between data types associated with the first system and data types associated with the second system. In these examples, receiving the first indication of the data types associated with a particular system may be based at least in part on the mapping. The process 900 may additionally, or alternatively, include determining a mapping between a first language associated with the first system and a second language associated with the second system. In these examples, generating the first model may comprise generating the first model using the second language based at least in part on the mapping.

The process 900 may additionally, or alternatively, include determining an amount of change of the probability of the outcome occurring based at least in part on utilizing a feature as an input to a given model. The process 900 may also include determining that the amount of change is greater than a threshold amount of change (e.g., more than 1% increase in probability) and utilizing the feature as the input based at least in part on the amount of change being greater than the threshold amount.

The process 900 may additionally, or alternatively, include determining that a data type impacts the probability by at least a threshold amount (e.g., more than 1% increase in probability) and may generate a directive to acquire data associated with the data type based at least in part on the determining. The process 900 may also include sending the directive to one or more associated systems, which may inform the systems of the importance of the data type to predicting a given outcome and/or may cause the systems to initiate acquisition of data of the data type.

Figure 10:
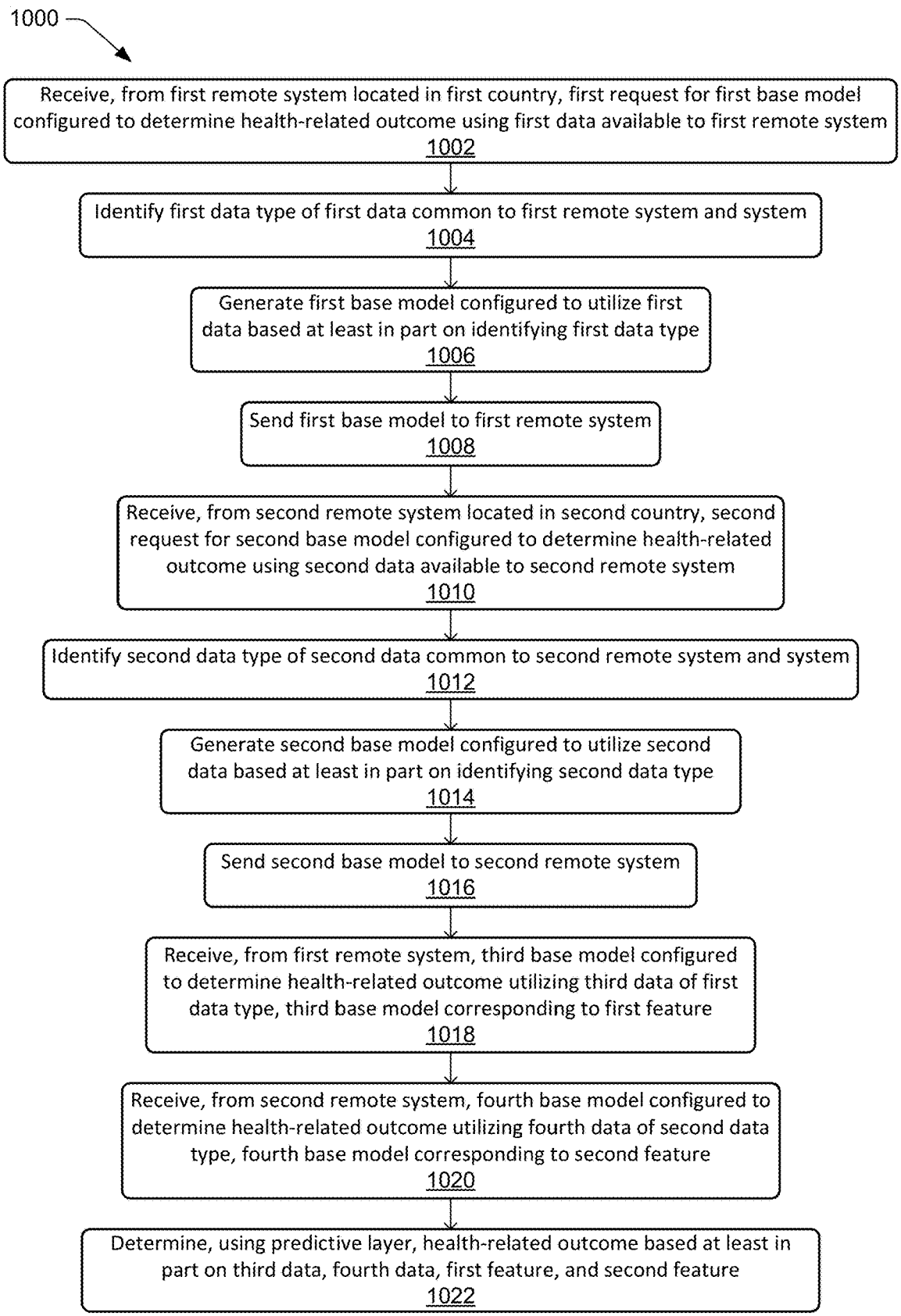
FIG. 10 illustrates a flow diagram of another example process for models utilizing siloed data.

FIG. 10 illustrates a flow diagram of another example process 1000 for models utilizing siloed data. The order in which the operations or steps are described is not intended to be construed as a limitation, and any number of the described operations may be combined in any order and/or in parallel to implement process 1000.

At block 1002, the process 1000 may include receiving, from a first remote system located in a first country, a first request for a first base model configured to determine a health-related outcome using first data available to the first remote system. Base models, as described herein, may be generated and/or utilized when three or more systems are associated, as described herein. Base models may be generated in response to a request for a base model from another system. For example, the second system and a third system may request a base model from the first system.

At block 1004, the process 1000 may include identifying a first data type of the first data common to the first remote system and the system. For example, the request, and/or other information available to the first system, may indicate the data and/or data types to be utilized by the first remote system. A common-data layer may store information indicating which data types are available to the systems. Using the common-data layer, a determination may be made as to the data types available to the first remote system that are also available to the system.

At block 1006, the process 1000 may include generating the first base model configured to utilize the first data based at least in part on identifying the first data type. A base model for the first remote system may be generated and fit based at least in part on overlapping data types between the system and the first remote system. A base model configured to utilize data of the overlapping data types may be generated by the base model component and may be fit by a fitting component. In examples, the base model may be utilized to predict the outcome using the data of the system.

At block 1008, the process 1000 may include sending the first base model to the first remote system. For example, the model may be packaged as a Docker image and may be transmitted to the first remote system in response to a pull request from the first remote system. Additionally, or alternatively, the model may be pushed to the first remote system from the system. The packaging may include operating-system-level virtualization, also described as containerization. Resource isolation features of the Linux kernel such as cgroups and kernel namespaces, and a union-capable file system, may be utilized to allow independent containers to run within a Linux instance, which may allow for operations without the use of virtual machines. In other examples, virtual machines may be generated and/or utilized. One or more APIs may be included and may be utilized by a system to predict outcomes with the model.

At block 1010, the process 1000 may include receiving, from a second remote system located in a second country, a second request for a second base model configured to determine the health-related outcome using second data available to the second remote system. Receiving the second request may be performed in the same or a similar manner as receiving the first request.

At block 1012, the process 1000 may include identifying a second data type of the second data common to the second remote system and the system. Identifying the second data type may be performed in the same or a similar manner as identifying the first data type.

At block 1014, the process 1000 may include generating the second base model configured to utilize the second data based at least in part on identifying the second data type. Generating the second base model may be performed in the same or a similar manner as generating the first base model.

At block 1016, the process 1000 may include sending the second base model to the second remote system. Sending the second base model may be performed in the same or a similar manner as sending the first base model.

At block 1018, the process 1000 may include receiving, from the first remote system, a third base model configured to determine the health-related outcome utilizing third data of the first data type, the third base model configured to generate a first feature. The feature may be an individual measurable property or characteristic of the observed outcome. The feature may be numeric and/or may include one or more strings and/or graphs. In examples, the feature may correspond to an explanatory variable, such as when statistical techniques are utilized when generating and/or utilizing predictive models. The features may be utilized as inputs by the predictive models of each system to predict the outcome, as described herein.

At block 1020, the process 1000 may include receiving, from the second remote system, a fourth base model configured to determine the health-related outcome utilizing fourth data of the second data type, the fourth base model configured to generate a second feature. By so doing, the system has provided base models to the first and second remote systems that utilize the common data types between systems. The fourth base model may be received in the same or a similar manner as the third base model.

At block 1022, the process 1000 may include determining, using a predictive layer, the health-related outcome based at least in part on the first data, the second data, the third data, the fourth data, the first feature, and the second feature. By so doing, the system may utilize the data available to it as well as the features received from the other two systems to predict the outcome. By adding the features to the analysis, the data from the two other systems is utilized in the analysis without the transfer of such data to the first system.

The process 1000 may additionally, or alternatively, include receiving an indication that a third remote system located in a third country, for example, has been associated with the system and determining that the third remote system has access to data of the first data type and the second data type. The process 1000 may also include generating, based at least in part on the data being of the first and second data type, a fifth base model configured to utilize the data to determine the health-related outcome. The fifth base model may be sent to the third remote system for use by the third remote system for predicting the outcome. The process 1000 may also include receiving, from the third remote system, a sixth base model configured to determine the health-related outcome utilizing the third data and the fourth data available to the system. The sixth base model may correspond to a feature, as described elsewhere herein. In these examples, determining the health-related outcome may be based at least in part on the feature.

The process 1000 may additionally, or alternatively, include identifying a second health-related outcome to determine and determining that the first data type and the third data type are relevant to the second health-related outcome. The process 1000 may also include determining that the third data type is associated with the first remote system and requesting a fifth base model from the first remote system. The fifth base model may be configured to determine the second health-related outcome based at least in part on data of the third data type. The process 1000 may also include receiving, from the first remote system, the fifth base model as a third feature and determining, using the predictive layer, the second health-related outcome based at least in part on the third data and the third feature.

The process 1000 may additionally, or alternatively, include determining a confidence at which the health-related outcome is determined based at least in part on the first feature and determining that the confidence exceeds a threshold confidence. The process 1000 may also include causing the second remote system to receive the first feature based at least in part on determining that the confidence exceeds the threshold confidence.

Figure 11:
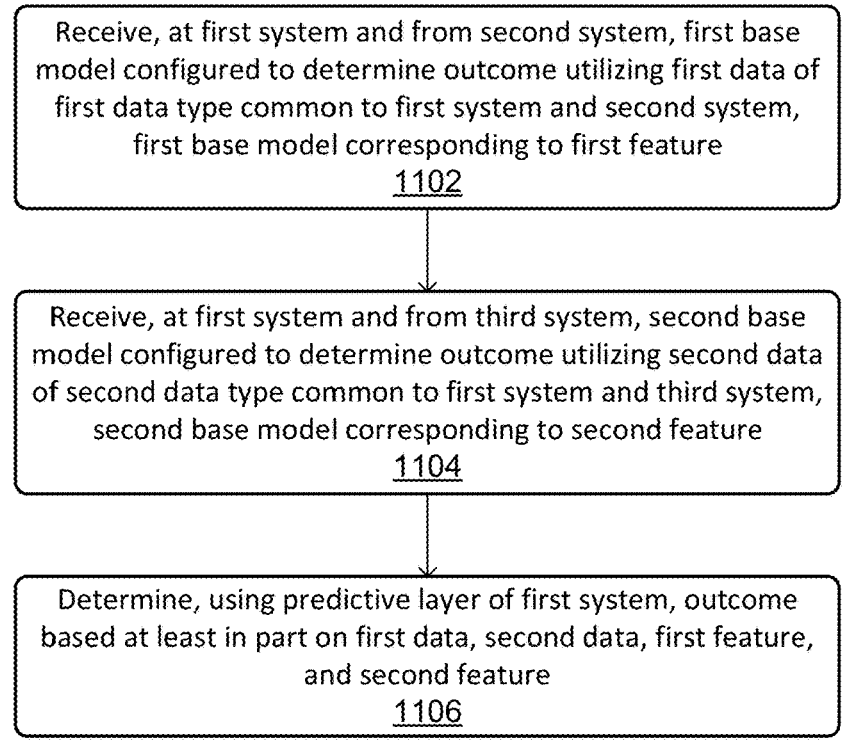
FIG. 11 illustrates a flow diagram of another example process for models utilizing siloed data.

FIG. 11 illustrates a flow diagram of another example process 1100 for models utilizing siloed data. The order in which the operations or steps are described is not intended to be construed as a limitation, and any number of the described operations may be combined in any order and/or in parallel to implement process 1100.

At block 1102, the process 1100 may include receiving, at a first system and from a second system, a first base model configured to determine an outcome utilizing first data of a first data type common to the first system and the second system, the first base model configured to generate a first feature. The feature may be an individual measurable property or characteristic of the observed outcome. The feature may be numeric and/or may include one or more strings and/or graphs. In examples, the feature may correspond to an explanatory variable, such as when statistical techniques are utilized when generating and/or utilizing predictive models. The features may be utilized as inputs by the predictive models of each system to predict the outcome, as described herein.

At block 1104, the process 1100 may include receiving, at the first system and from a third system, a second base model configured to determine the outcome utilizing second data of a second data type common to the first system and the third system, the second base model configured to generate a second feature. Receiving the second base model may be performed in the same or a similar manner as receiving the first base model.

At block 1106, the process 1000 may include determining, using a predictive layer of the first system, the outcome based at least in part on the first data, the second data, the first feature, and the second feature. A base model for the first system may be fit based at least in part on overlapping data types between the first system and the system sending the base model. In examples, the base model may be utilized to predict the outcome using the data of the system as well as features received from associated systems.

The process 1100 may additionally, or alternatively, include receiving an indication that a fourth system has been associated with the first system and determining that the fourth system has access to third data of the first data type and the second data type. The process 1100 may also include generating, based at least in part on the third data being of the first data type and the second data type, a third base model configured to utilize the third data to determine the outcome. The process 1100 may also include sending the third base model to the fourth system.

The process 1100 may additionally, or alternatively, include identifying a second outcome to determine and determining that the first data type and the third data type are relevant to the second outcome. The process 1100 may also include determining that the third data type is associated with the second system and requesting a third base model from the second system. The third base model may be configured to determine the second outcome based at least in part on data of the third data type. The process 1100 may also include receiving, from the second system, the third base model as a feature and determining, using the predictive layer, the second outcome based at least in part on the third data and the third feature.

The process 1100 may additionally, or alternatively, include determining a confidence at which the outcome is determined based at least in part on the first feature and determining that the confidence exceeds a threshold confidence. The process 1100 may also include causing the third system to receive the first feature based at least in part on determining that the confidence exceeds the threshold confidence.

The process 1100 may additionally, or alternatively, include determining a first confidence at which the first system determines the outcome using the first data, the second data, the first feature, and the second feature. The process 1100 may also include receiving an indication of a second confidence at which the outcome is determined by the second system using third data of a third data type and determining that the second confidence is greater than the first confidence. The process 1100 may also include causing the first system to acquire fourth data of the third data type based at least in part on determining that the second confidence is greater than the first confidence.

The process 1100 may additionally, or alternatively, include determining, using the predictive layer, a second instance of the outcome without using the second data and determining a first confidence at which the first instance of the outcome is determined. The process 1100 may also include determining a second confidence at which the second instance of the outcome is determined and determining that the second confidence is within a threshold confidence range of the first confidence. The process 1100 may also include removing the second data based at least in part on determining that the second confidence is within the threshold confidence range.

Figure 12:
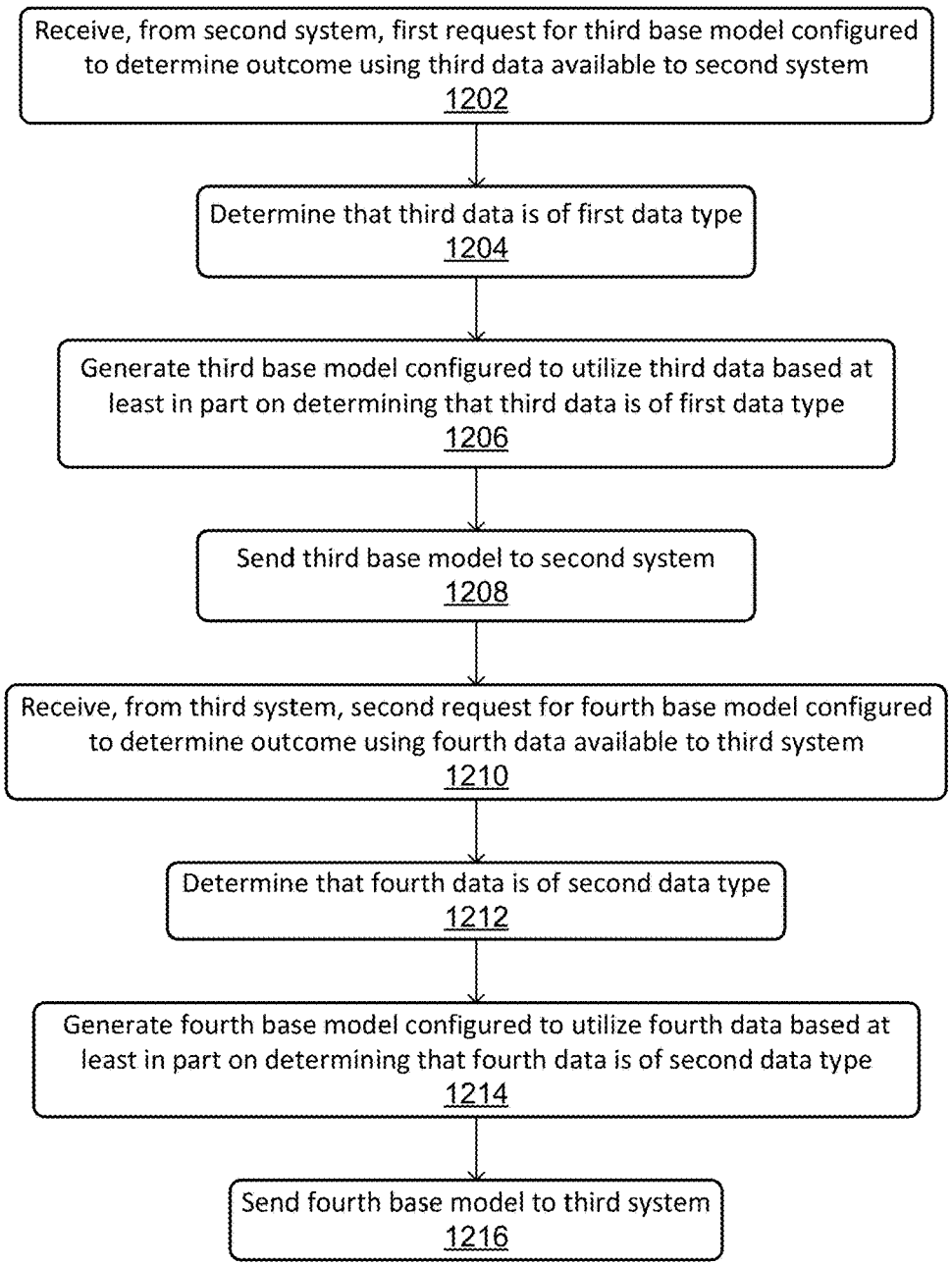
FIG. 12 illustrates a flow diagram of an example process for generation and sharing of models.

FIG. 12 illustrates a flow diagram of another example process 1200 for generation and sharing of models. The order in which the operations or steps are described is not intended to be construed as a limitation, and any number of the described operations may be combined in any order and/or in parallel to implement process 1200.

At block 1202, the process 1200 may include receiving, from the second system, a request for a third base model configured to determine the outcome using third data available to the second system. Base models, as described herein, may be generated and/or utilized when three or more systems are associated, as described herein. Base models may be generated in response to a request for a base model from another system. For example, the second system and a third system may request a base model from the first system.

At block 1204, the process 1200 may include determining that the third data is of the first data type. For example, the request, and/or other information available to the first system, may indicate the data and/or data types to be utilized by the second system. A common-data layer may store information indicating which data types are available to the systems. Using the common-data layer, a determination may be made as to the data types available to the second system that are also available to the first system.

At block 1206, the process 1200 may include generating the third base model configured to utilize the third data based at least in part on determining that the third data is of the first data type. Generating the third base model may be performed in the same or a similar manner as generation of other base models, such as described with respect to FIG. 11.

At block 1208, the process 1200 may include sending the third base model to the second system. For example, the base model may be packaged as a Docker image and may be transmitted to the second system in response to a pull request from the second system. Additionally, or alternatively, the model may be pushed to the second system from the first system. The packaging may include operating-system-level virtualization, also described as containerization. Resource isolation features of the Linux kernel such as cgroups and kernel namespaces, and a union-capable file system, may be utilized to allow independent containers to run within a Linux instance, which may allow for operations without the use of virtual machines. In other examples, virtual machines may be generated and/or utilized. One or more APIs may be included and may be utilized by a system to predict outcomes with the model.

At block 1210, the process 1200 may include receiving, from the third system, a request for a fourth base model configured to determine the outcome using fourth data available to the third system. The second request may be received in the same or a similar manner as the first request.

At block 1212, the process 1200 may include determining that the fourth data is of the second data type. For example, the request, and/or other information available to the first system, may indicate the data and/or data types to be utilized by the third system. A common-data layer may store information indicating which data types are available to the systems. Using the common-data layer, a determination may be made as to the data types available to the third system that are also available to the first system.

At block 1214, the process 1200 may include generating the fourth base model configured to utilize the fourth data based at least in part on determining that the fourth data is of the second data type. Generation of the fourth base model may be performed in the same or a similar manner as generation of the third base model.

At block 1216, the process 1200 may include sending the fourth base model to the third system. Sending of the fourth base model may be performed in the same or a similar manner as sending of the third base model.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A system comprising:
   one or more processors; and
   computer-readable media storing first computer-executable instructions that, when executed by the one or more processors, cause the one or more processors to perform operations comprising:

receiving, from a first source associated with a first country, first data associated with health of a first individual, the first data corresponding to a first data type;

receiving, from at least one of the first source or a second source associated with the first country, second data associated with the health of the first individual, the second data corresponding to a second data type;

receiving, from a remote system associated with a second country, a first indication that the remote system is associated with:

third data associated with health of a second individual, the third data corresponding to the first data type, the third data being restricted from transfer from the remote system; and fourth data associated with the health of the second individual, the fourth data corresponding to a third data type, the fourth data being restricted from transfer from the remote system;

receiving a second indication of a health-related outcome to be determined with respect to the second individual;

sending, to the remote system and based at least in part on the third data and the fourth data being restricted from transfer, a predictive-layer configuration including pseudo code configured for use by the remote system to generate a first predictive layer configured to accept the third data and the fourth data and to determine a first probability of the healthrelated outcome occurring with respect to the second individual;

generating, based on the remote system being associated with the third data and receiving the first data, a second predictive layer configured to accept the first data and to determine a second probability, based on the first data, of the health-related outcome occurring with respect to the first individual;

sending the second predictive layer to the remote system, the second predictive layer configured to generate a first feature configured as an input to the first predictive layer;

receiving, from the remote system, a third predictive layer configured to generate a second feature;

generating a fourth predictive layer configured to accept the first data, the second data, and the second feature; and determining a third probability of the health-related outcome occurring with respect to the first individual based on the fourth predictive layer.

2. The system of claim 1, the operations further comprising:

generating a serialized object corresponding to the second predictive layer, the serialized object including:
a coefficient mapping for the first data type; and
a resource configured to allow the remote system to utilize the coefficient mapping with respect to the third data.

3. The system of claim 1, wherein the second feature comprises a serialized object corresponding to the third predictive layer, and the operations further comprise ensembling the serialized object with the fourth predictive layer.

4. The system of claim 1, the operations further comprising fitting the fourth predictive layer for the first data, the second data, and the second feature based on historical data associated with the first data type and the second data type.

5. A method, comprising:

receiving, at a first system and from a second system that is remote from the first system and is associated with a second country that differs from a first country of the first system, an indication that the second system is associated with:

first data of a first data type; and second data of a second data type, the second data being restricted from transfer from the second system;

generating, based at least in part on the indication, a first predictive layer configured to determine whether a health-related outcome occurs;

sending the first predictive layer to the second system, wherein the first predictive-layer includes pseudo code configured for use by the second system to generate a second predictive layer;

receiving, from the second system, a second predictive layer configured to generate a feature associated with the first data;

generating, based on the second system being associated with the first data, a third predictive layer configured to accept the first data and the second data; and determining, using the third predictive layer whether the health-related outcome occurs based at least in part on third data of the first data type and the feature.

6. The method of claim 5, further comprising:

generating a serialized object corresponding to the second predictive layer, the serialized object including:
a coefficient mapping for the first data type; and
a resource configured to allow the second system to utilize the coefficient mapping with respect to the first data.

7. The method of claim 5, wherein the feature comprises a serialized object corresponding to the second predictive layer and the method further comprises ensembling the serialized object with the third predictive layer.

8. The method of claim 5, further comprising fitting, based at least in part on historical data associated with the first data type and a third data type, the third predictive layer for:

the third data;
fourth data associated with the third data type; and
the feature.

9. The method of claim 5, further comprising:

determining a mapping between data types associated with the first system and data types associated with the second system; and wherein receiving the indication is based at least in part on the mapping.

10. The method of claim 5, wherein the first system is configured in a first language and the second system is configured in a second language, and the method further comprises:

determining a mapping between the first language and the second language; and wherein generating the first predictive layer comprises generating the first predictive layer using the second language based at least in part on the mapping.

11. The method of claim 5, further comprising:

generating the third predictive layer;
determining a confidence associated with determining whether the health-related outcome occurs based at least in part on utilizing the feature as an input to the third predictive layer;
determining that the confidence is greater than a threshold confidence; and utilizing the feature as the input based at least in part on the confidence being greater than the threshold confidence.

12. The method of claim 5, further comprising:
determining that the third data type impacts the health-related outcome occurring by at least a threshold amount;
generating a directive to acquire data of the third data type; and
send the directive to the second system.

13. A system, comprising:
one or more processors; and
computer-readable media storing first computer-executable instructions that, when executed by the one or more processors, cause the one or more processors to perform operations comprising:
receiving, at a first system and from a second system that is remote from the first system and is associated with a second country that differs from a first country of the first system, an indication that the second system is associated with first data of a first data type, and second data of a second data type, the second data being restricted from transfer from the second system;
generating, based at least in part on the indication, a first model predictive layer configured to determine whether a health-related outcome occurs;
sending the first predictive layer to the second system, wherein the first predictive layer includes pseudo code configured for use by the second system to generate a second predictive layer;
receiving, from the second system, the second predictive layer configured to generate a feature associated with the first data;
generating, based on the second system being associated with the first data, a third predictive layer configured to accept the first data and the second data to determine a second probability; and
determining, using the third predictive layer whether the health-related outcome occurs based at least in part on third data of the first data type and the feature.

14. The system of claim 13, the operations further comprising:
generating a serialized object corresponding to the second predictive layer, the serialized object including:
a coefficient mapping for the first data type; and
a resource configured to allow the second system to utilize the coefficient mapping with respect to the first data;
wherein sending the second predictive layer comprises sending the serialized object to the second system.

15. The system of claim 13, wherein the feature comprises a serialized object corresponding to the second predictive layer, and the operations further comprise ensembling the serialized object with the third predictive layer.

16. The system of claim 13, the operations further comprising fitting, based at least in part on historical data associated with the first data type and a third data type, the third predictive layer for:
the third data;
fourth data associated with the third data type; and
the feature.

17. The system of claim 13, the operations further comprising:
determining a mapping between data types associated with the first system and data types associated with the second system; and
wherein receiving the indication is based at least in part on the mapping.

18. The system of claim 13, wherein the first system is configured in a first language and the second system is configured in a second language, and the method further comprises:
determining a mapping between the first language and the second language; and
wherein generating the first predictive layer comprises generating the first predictive layer using the second language based at least in part on the mapping.

19. The system of claim 13, the operations further comprising:
generating the third predictive layer;
determining a confidence associated with determining whether the health-related outcome occurs based at least in part on utilizing the feature as an input to the third predictive layer;
determining that the confidence is greater than a threshold confidence; and
utilizing the feature as the input based at least in part on the confidence being greater than the threshold confidence.

20. The system of claim 13, the operations further comprising:
determining that the third data type impacts whether the health-related outcome is determined to occur by at least a threshold amount;
generating a directive to acquire data of the third data type; and
send the directive to the second system.

* * * * *